US008690828B2

(12) United States Patent
Fujioka et al.

(10) Patent No.: US 8,690,828 B2
(45) Date of Patent: Apr. 8, 2014

(54) SYRINGE DRIVE DEVICE

(75) Inventors: Soichiro Fujioka, Osaka (JP); Tohru Nakamura, Osaka (JP); Osamu Mizuno, Osaka (JP); Akinobu Okuda, Nara (JP); Akihiro Ohta, Osaka (JP)

(73) Assignee: Panasonic Corporation, Osaka (JP)

( * ) Notice: Subject to any disclaimer, the term of this patent is extended or adjusted under 35 U.S.C. 154(b) by 86 days.

(21) Appl. No.: 13/375,309

(22) PCT Filed: Jul. 22, 2010

(86) PCT No.: PCT/JP2010/004698
§ 371 (c)(1),
(2), (4) Date: Nov. 30, 2011

(87) PCT Pub. No.: WO2011/010467
PCT Pub. Date: Jan. 27, 2011

(65) Prior Publication Data
US 2012/0078180 A1     Mar. 29, 2012

(30) Foreign Application Priority Data

Jul. 23, 2009   (JP) ................................. 2009-171703

(51) Int. Cl.
*A61M 37/00*      (2006.01)
(52) U.S. Cl.
USPC ....................................................... 604/131
(58) Field of Classification Search
USPC ......... 604/131, 151, 152, 154, 155, 207, 218, 604/224, 228
See application file for complete search history.

(56) References Cited

U.S. PATENT DOCUMENTS 5,269,762 A * 12/1993 Armbruster et al. .......... 604/155
7,182,751 B2   2/2007 Nemoto et al.
7,192,417 B2 *  3/2007 Thompson et al. ........... 604/154

FOREIGN PATENT DOCUMENTS

| CN | 1572334 | 2/2005 |
|---|---|---|
| JP | 5-42213 | 2/1993 |
| JP | 6-7440 | 1/1994 |
| JP | 2004-121467 | 4/2004 |

OTHER PUBLICATIONS

International Search Report issued Aug. 24, 2010 in International (PCT) Application No. PCT/JP2010/004698.
English translation of International Preliminary Report on Patentability issued Feb. 16, 2012 in International (PCT) Application No. PCT/JP2010/004698.
Chinese Office Action issued May 15, 2013 in corresponding Chinese Application No. 201080024630.2.

* cited by examiner

*Primary Examiner* — Theodore Stigell
(74) *Attorney, Agent, or Firm* — Wenderoth, Lind & Ponack, L.L.P.

(57) ABSTRACT

A syringe drive device 1 includes a cylinder holding section 3 configured to detachably hold a cylinder 201, a piston manipulating section 4 detachably coupled with a piston, and a piston drive section 5 including racks 31A and 31B coupled with the piston manipulating section 4 and configured to move the piston manipulating section 4 so that a piston 202 is moved in a push-in direction or a pull-out direction. A cylinder 200A having a given capacity (for example, 50 cc) is directly loaded in the syringe drive device 1 with no adapter therebetween. A syringe 200C having a different capacity (for example, 20 cc) is loaded in the syringe drive device 1 by means of a cylinder adapter 81 and a piston adapter 82.

18 Claims, 15 Drawing Sheets

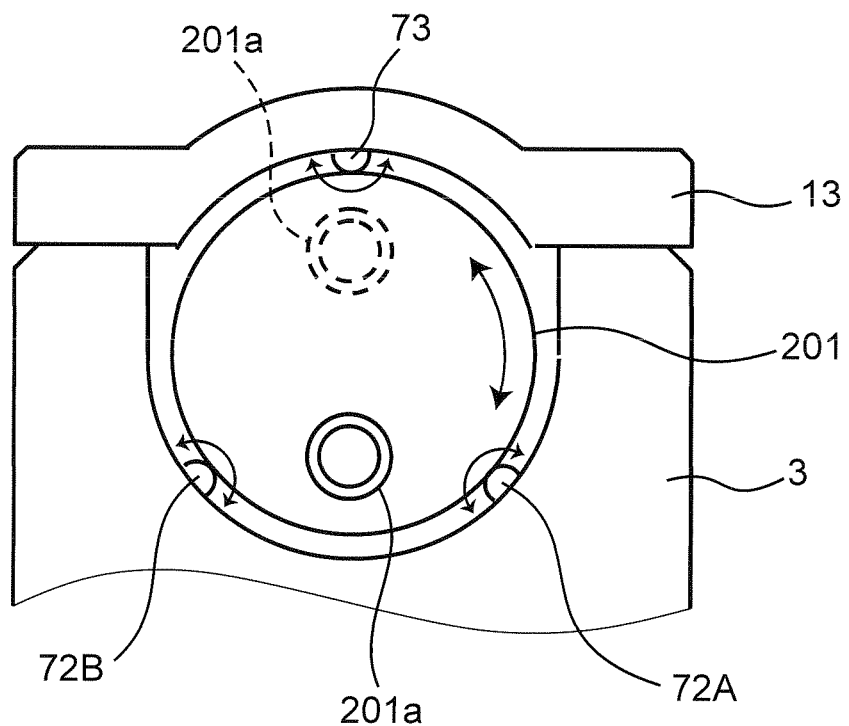

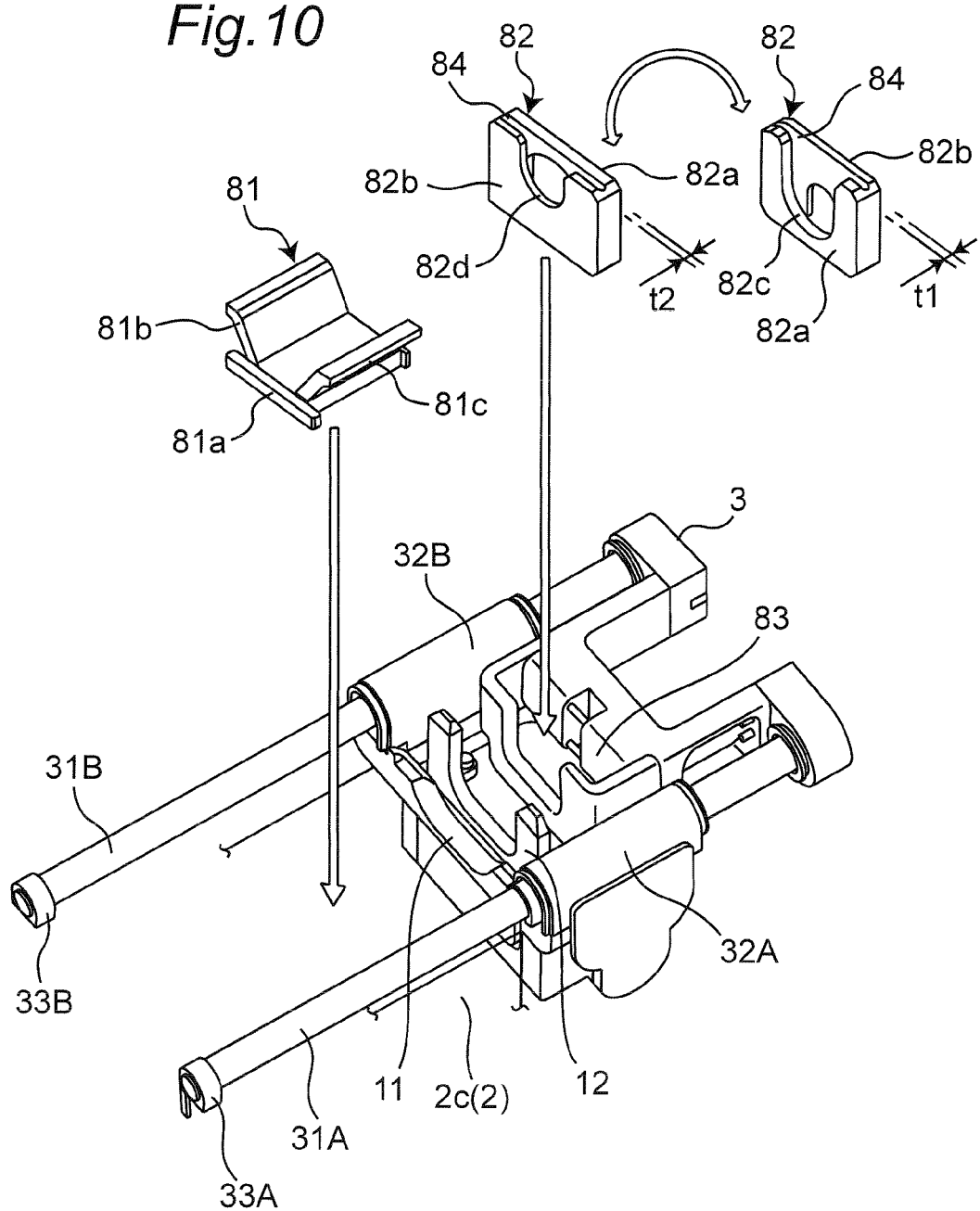

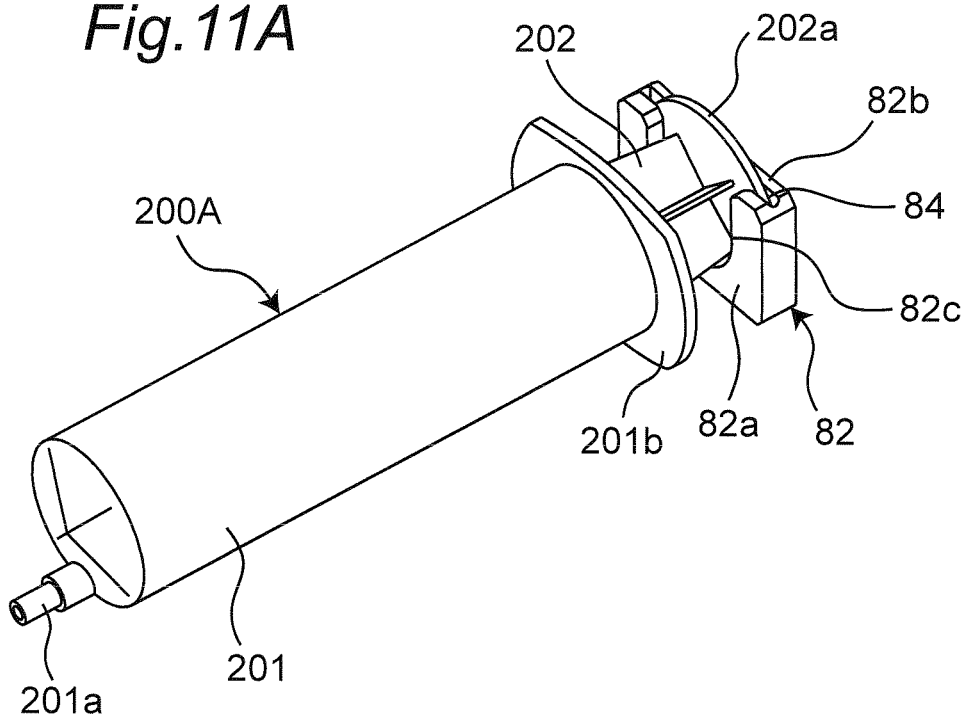
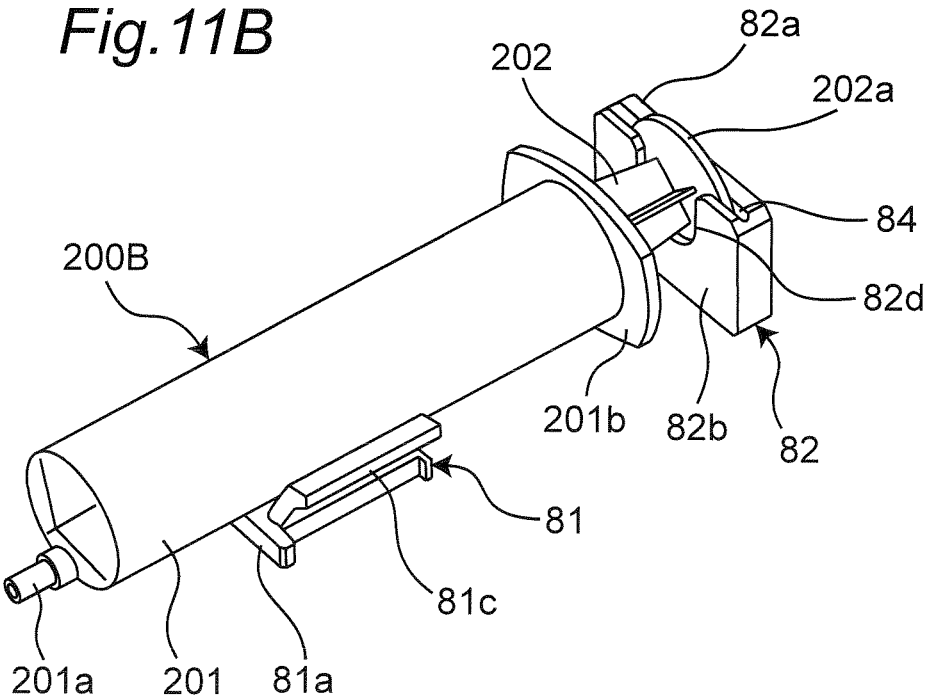

SYRINGE DRIVE DEVICE

TECHNICAL FIELD

The present invention relates to a syringe drive device configured to move a piston (suctioning piece or plunger) of a syringe, which is used in a medication dispensing operation, such as a mixing operation to prepare an injection solution or a drip-feed solution, relative to the cylinder (outer tube or barrel).

BACKGROUND ART

In healthcare facilities, a syringe is conventionally used in a medication dispensing operation, such as a mixing operation to prepare an injection solution or a drip-feed solution. A plurality of medicinal agents contained in medicinal solution containers, such as vial containers, are suctioned by the syringe and then mixed in the syringe to dispense a pharmaceutical preparation. The dispensed pharmaceutical preparation is stored in a container such as an infusion bag.

The syringe includes a cylinder of tubular shape having a solution port on one end and an opening on the other end thereof, and a piston inserted into the cylinder through the opening. When the medicinal agent is suctioned by the syringe from the medicinal solution container, the piston is moved in a direction where the piston is pulled out from the cylinder. When the medicinal agent is injected into the container, for example, infusion bag, the piston is moved in a direction where the piston is pushed into the cylinder.

To suction the medicinal agent from the medicinal solution container into the syringe, it is necessary to continuously drive the piston in the pull-out direction against a negative pressure. To inject the medicinal agent from the syringe into the infusion bag, it is necessary to continuously drive the piston in the push-in direction against a positive pressure generated by, for example, a filter interposed in a passage therebetween. A reaction force generated when the piston is driven against the negative pressure or the positive pressure is significantly large, possibly as large as a few 10N. During the dispensing operation, an operator conventionally manipulates the piston of the syringe held with one hand, while holding the medicinal solution container with the other hand. Depending on the circumstances, the operator may have to suitably retain a positional relationship between the medicinal solution container and the syringe relative to each other. It is such an annoying work to manipulate the piston against such a large reaction force as a few 10N while holding the syringe at a certain angle with one hand.

The Patent Document 1 discloses a syringe drive device to help an operator to manipulate a syringe when a constant flow of medicinal agent is administered to human body.

Referring to FIG. 15, a syringe drive device 600 disclosed in the Patent Document 1 includes a cylinder holding section 603 which holds a cylinder 602 of a syringe 601, and a piston drive section (slider) 605 which axially drives a piston 604 relative to the cylinder 602 held by the cylinder holding section 603. When a feed screw thread 608 is driven by a motor (not illustrated in the drawings), a driven member 607 engaged with the feed screw thread 608 linearly moves. The piston drive section 605 is coupled with the driven member 607 by means of a coupling member 606 to thereby drive the piston 604 in a direction where the driven member 607 moves.

There are syringes having different storage capacity, for example, from 50 cc, 30 cc, to 20 cc. The syringes thus having different storage capacities are different from one another in shape, more specifically, length of cylinder, length of piston, and dimension from outer periphery of cylinder to solution port (height dimension of solution port). Some syringes having an equal storage capacity may have different shapes because they were manufactured by different manufacturers or manufactured according to different technical standards. When the operator uses the syringe drive device to suction or inject the medicinal solution while holding the syringe with one hand and the medicinal solution container with the other, it is important that various syringes having different shapes are usable and the operator can equally handle the syringe drive device even if the syringe having different shape is used. If there is variability when the syringes respectively having different storage capacities are loaded and used in the syringe drive device in where a tip of an injection needle attached to the syringe is situated, the workability is significantly deteriorated. The device disclosed in the Patent Document 1 was not particularly designed to address syringes formed in different shapes and equal usability in this case.

CITATION LIST

Patent Document

[PATENT DOCUMENT 1] Unexamined Japanese Patent Application Publication No. 05-42213

SUMMARY OF THE INVENTION

Technical Problem

The present invention provides a syringe drive device that can be loaded with syringes formed in different shapes.

Solution Problem

The present invention provides a syringe drive device, including: a cylinder holding section configured to detachably hold a cylinder of a syringe; a piston manipulating section detachably engaged with a piston of the syringe having an end inserted in the cylinder; a piston drive section configured to move the piston manipulating section along a central axis of the piston to thereby move the piston in a direction where the piston is pushed into the syringe or a direction where the piston is pulled out from the syringe; and a cylinder adapter loaded in the cylinder holding section and configured to detachably hold a cylinder of a second syringe having a shape different to a cylinder of a first syringe directly held by the cylinder holding section, the cylinder adapter equally retaining a position of the cylinder between the first and second syringes. The cylinder adapter equally retains a position of the cylinder on an end side thereof between the first and second syringes. The cylinder adapter equally retains a height position of a solution port provided in an end of the cylinder between the first and second syringes. The syringe drive device may further include a piston adapter having an end detachably coupled with the piston of the second syringe and another end detachably coupled with the piston manipulating section when the cylinder of the second syringe is loaded in the cylinder holding section by means of the cylinder adapter.

Effect of the Invention

The syringe drive device according to the present invention is provided with the cylinder adapter capable of equally retaining the positions of any syringes even when the syringe having different shapes are loaded therein. The syringe drive device according to the present invention can be used with the syringes having different shapes and improves the workability. When the syringes having the cylinder adapter with a different shape are loaded, tips of injection needles attached to these syringes are situated at a substantially equal position. This improves the workability in suctioning a medicinal solution from a medicinal solution container, for example, vial container, and injecting a medicinal solution into a container, for example, infusion bag. The syringe drive device according to the present invention can skillfully and readily manipulate a plurality of different syringes formed in different shapes because of such a factor as different storage capacities, different manufacturers, or different technical standards. The syringe drive device can largely alleviate the work burden of any healthcare professional such as nurse or pharmacist engaged in a medication dispensing operation.

BRIEF DESCRIPTION OF THE DRAWINGS

FIG. 9 is an illustration of the syringe drive device when viewed from the direction of IX-IX line in FIG. 1 (modified embodiment).

FIG. 10 is a perspective view of main sections in a syringe drive device according to an embodiment 2 of the present invention.

FIG. 11A is a perspective view of the adapter and a syringe having the storage capacity of 50 cc in the syringe drive device according to the embodiment 2.

FIG. 11B is a perspective view of the adapter and a syringe having the storage capacity of 30 cc in the syringe drive device according to the embodiment 2.

DESCRIPTION OF EMBODIMENT

Figure 1:
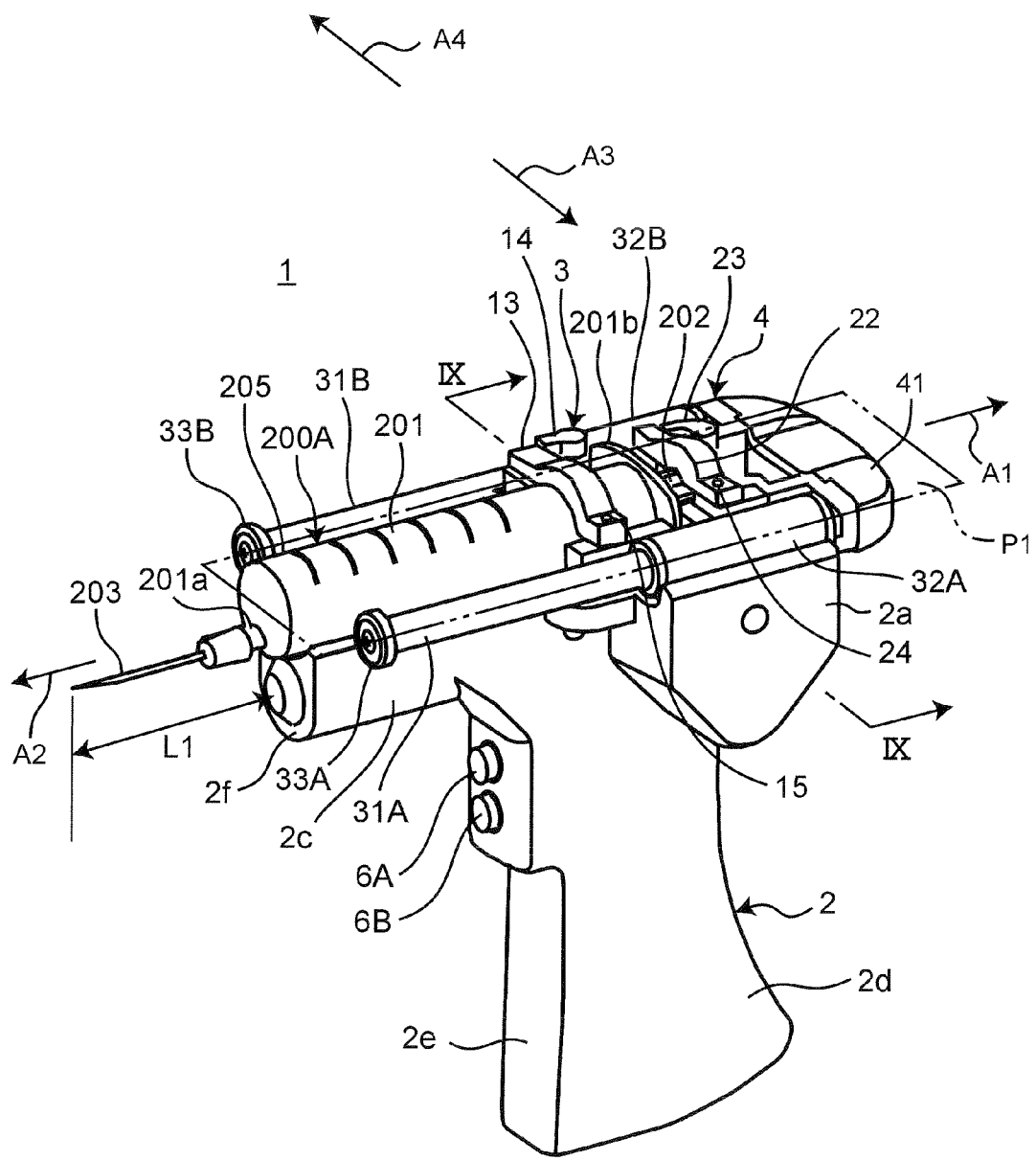
FIG. 1 is a perspective view of a syringe drive device (where no adapter is used) according to an embodiment 1 of the present invention.

Hereinafter, embodiments of the present invention are described referring to the accompanied drawings. The same structural elements are simply illustrated with the same reference numerals to omit redundant description.

Figure 14:
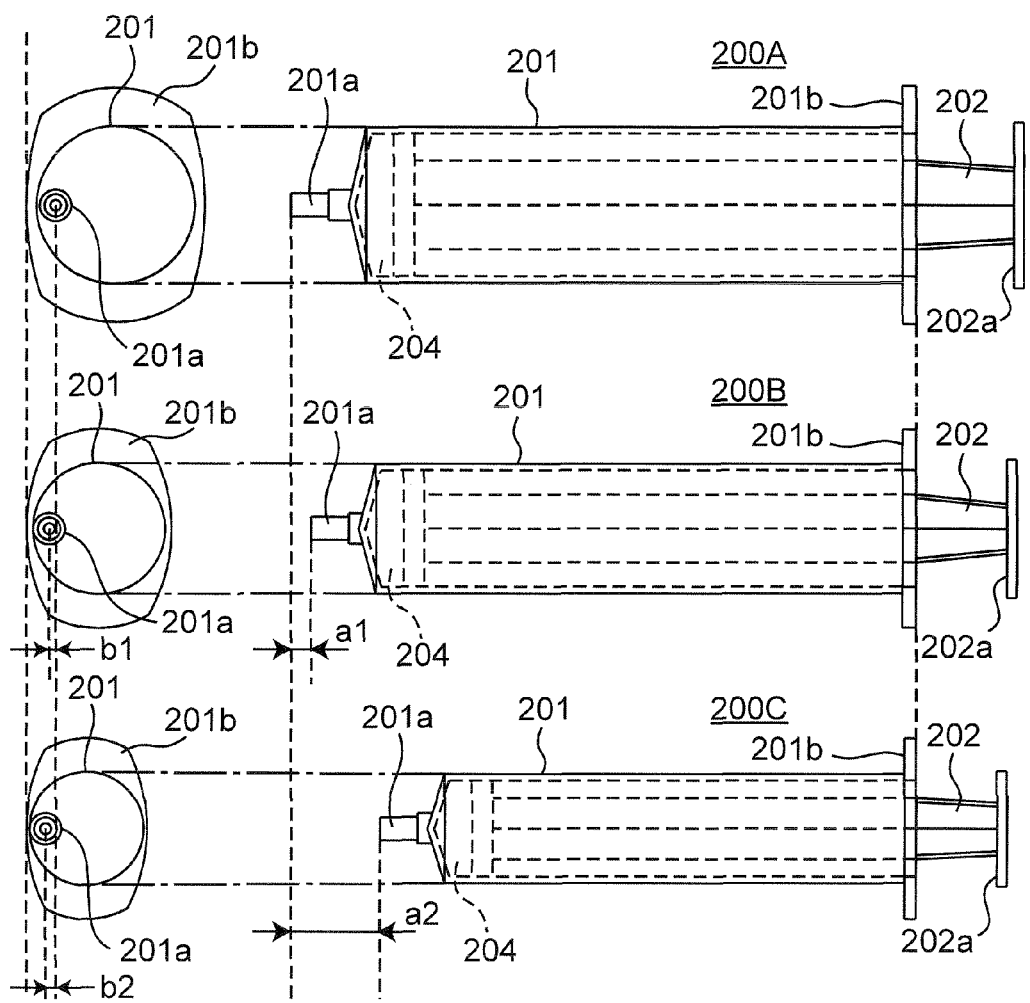
FIG. 14 is a plan view and a front view comparatively illustrating syringes respectively having the storage capacities of 50 cc, 30 cc, and 20 cc.
Figure 15:
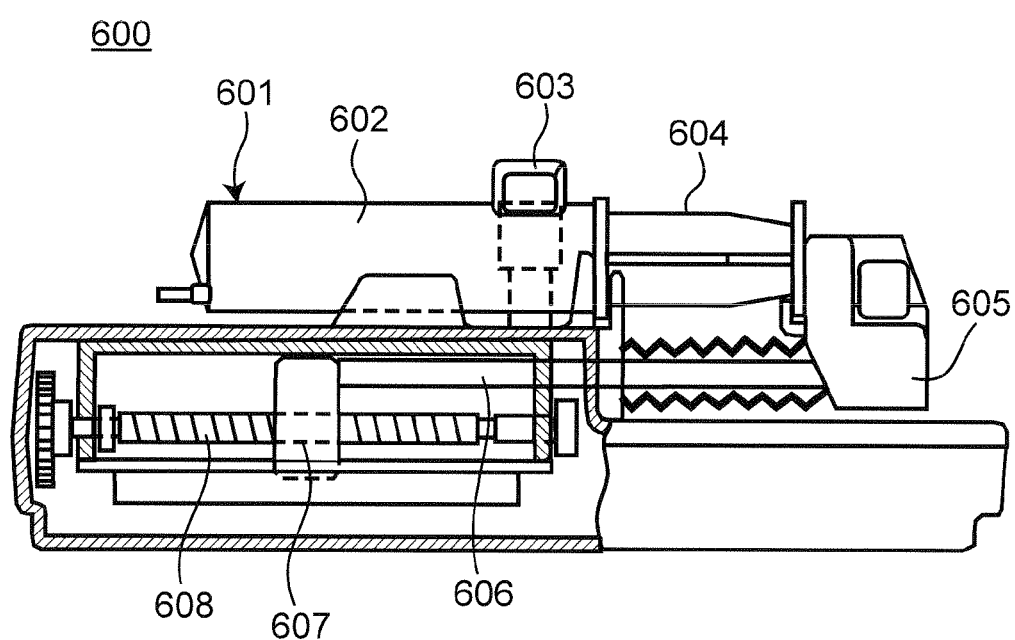
FIG. 15 is a longitudinal sectional view of a conventional syringe drive device.

First, syringes are described. FIG. 14 illustrates a syringe 200A having a large storage capacity (for example, 50 cc), a syringe 200B having an intermediate storage capacity (for example, 30 cc), and a syringe 200C having a small storage capacity (for example, 20 cc). These syringes 200A to 200C each includes a cylinder 201 having a solution port 201a equipped with an injection needle 203 (see FIG. 1) in an end thereof, and a piston 202 having an end provided with a gasket 204 inserted in a cylinder 201 through an opening on the opposite side of the solution port 201a. The cylinder 201 has scale marks 205 thereon (see FIG. 1). A flange portion 201b is provided on an end of the cylinder 201 near the opening, and a jaw portion 202a is provided on a rear end of the piston 202. The cylinders 201 of the syringes 200A to 200C with different storage capacities respectively have different shapes. The illustrated examples respectively have ends of the cylinders 201 at different positions when measured on the basis of the respective flange portions 201b as illustrated with reference symbols α1 and α2. Similarly, positions of the gaskets 204 of the syringes 200A to 200C (initial reference positions) when their pistons 202 are pushed into the respective cylinders 201 to the far end (initial positions) are different from one another when measured on the basis of the respective flange portions 201b. As illustrated with reference symbols b1 and b2, height positions of the solution ports 201a, which are respectively measured from outer peripheries of the cylinders 201, are also different from one another. Moreover, positions of the jaw portions 202a, which are respectively measured on the basis of the flange portions 201b of the cylinders 201 when the pistons 202 are at the initial positions, are different from one another. Other than the different storage capacities, shapes of the cylinders and/or positions of the jaw portions provided in the pistons are possibly different because of such a factor as different manufacturers or different manufacturing technical standards.

[Embodiment 1]

Figure 2:
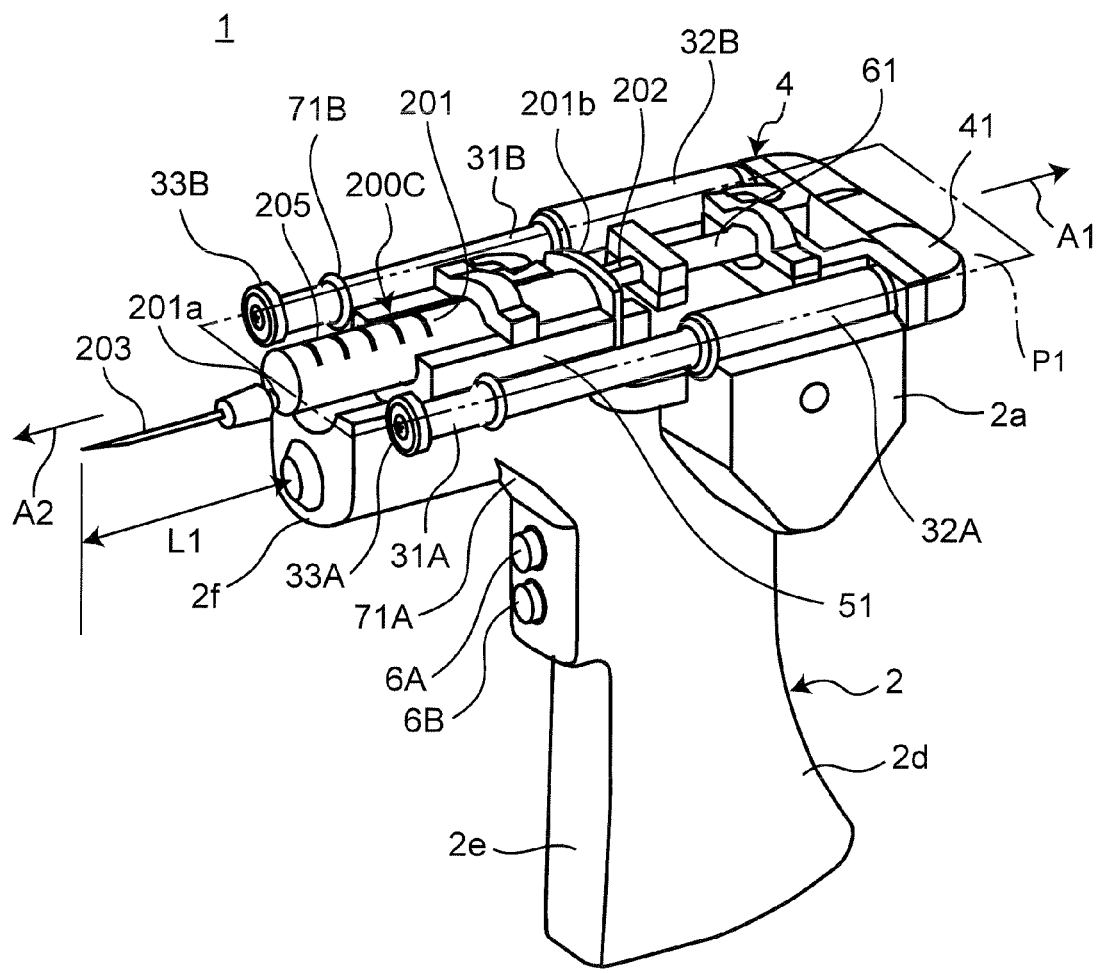
FIG. 2 is a perspective view of the syringe drive device (where an adapter is used) according to the embodiment 1.

FIGS. 1 and 2 illustrate a syringe drive device 1 of mobile type according to an embodiment 1 of the present invention. The syringe drive device 1 drives a piston of a syringe used in a medication dispensing operation, such as a mixing operation to prepare an injection solution or a drip-feed solution. The syringe drive device 1 can be loaded with any of a large syringe 200A (FIG. 1) and a small syringe 200C (FIG. 2) in which cylinders 201 respectively have different shapes and jaw portions 202a of pistons 202 at the initial positions are differently located. When the small syringe 200C is loaded in the syringe drive device 1, a cylinder adapter 51 and a piston adapter 61 which are described later are used.

Hereinafter is described a basic structure of the syringe drive device 1 where neither of the cylinder adapter 51 nor the piston adapter 61 is used (no adapter is used). In the description given below, left side of the syringe drive device 1 on the drawing of FIG. 1 may be called front side (side illustrated with arrow A2), right side thereof may be called rear side (side illustrated with arrow A1), near side thereof may be called left side (side illustrated with arrow A3), and far side thereof may be called right side (side illustrated with arrow A4).

Figure 3:
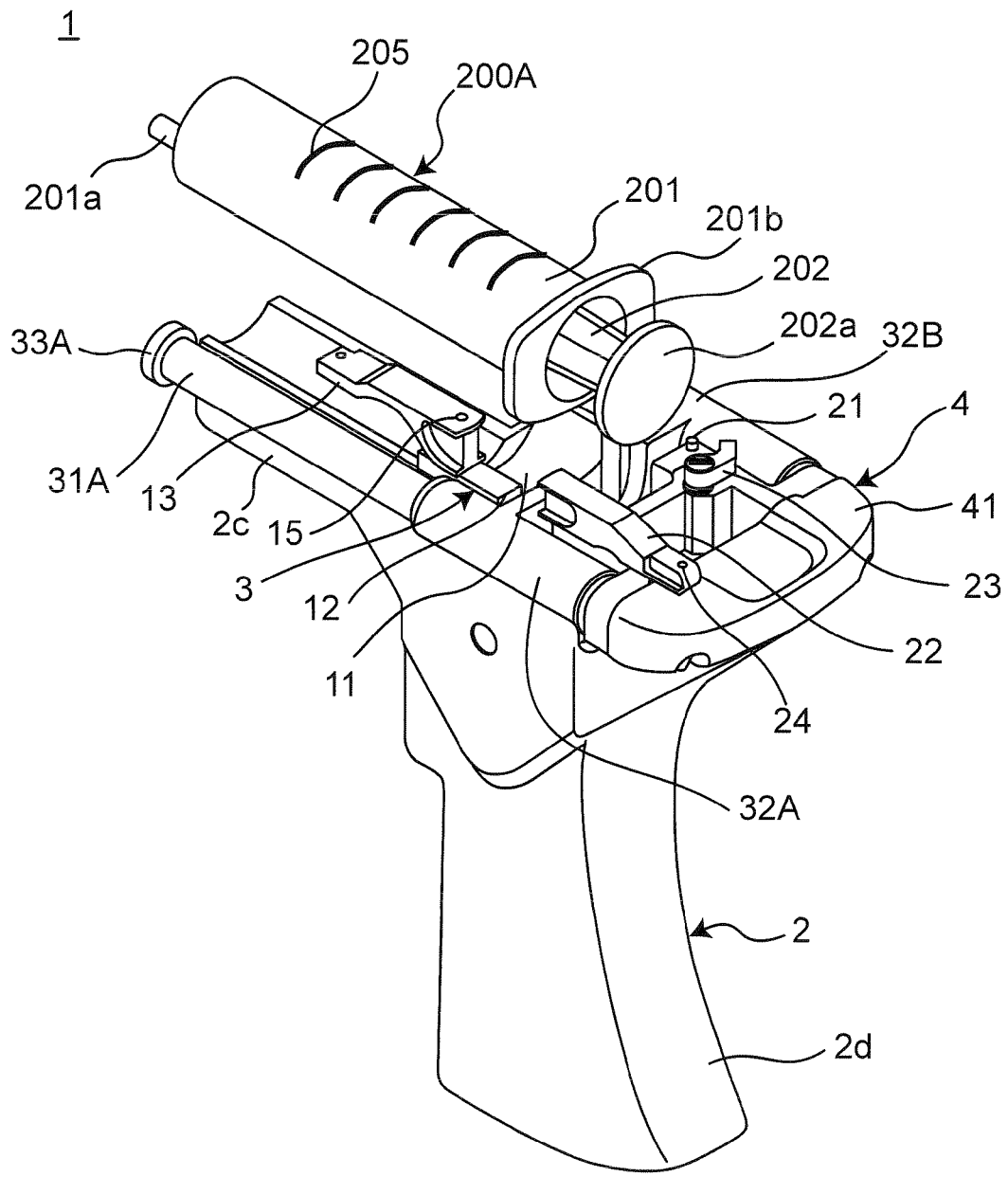
FIG. 3 is a perspective view of the syringe drive device (where no adapter is used) according to the embodiment 1 from which a syringe is removed.
Figure 4:
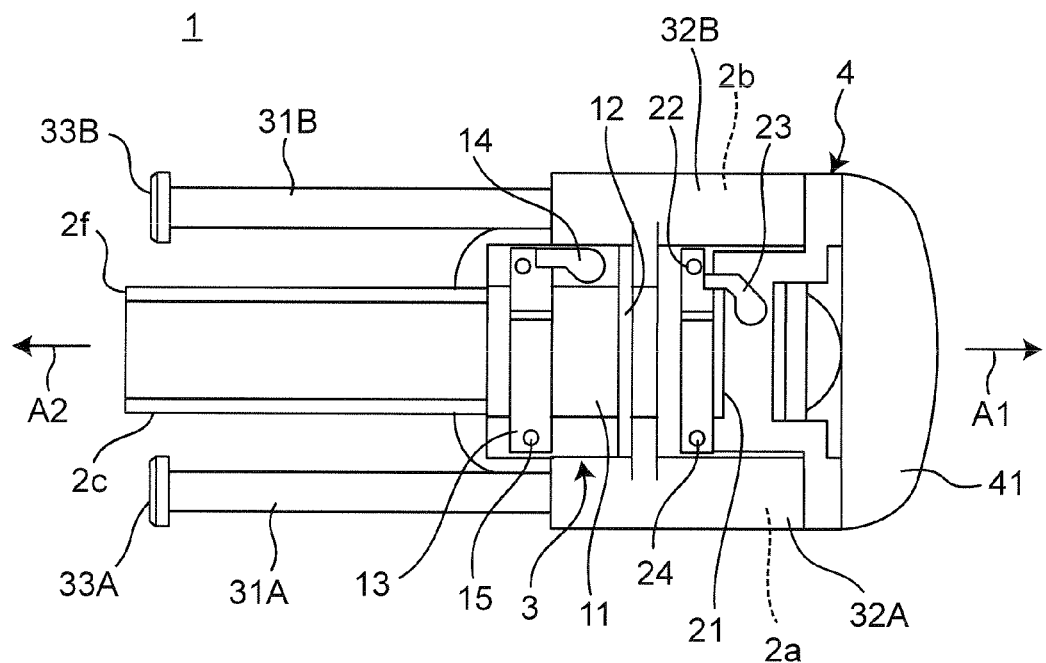
FIG. 4 is a plan view of the syringe drive device (where no adapter is used) according to the embodiment 1.

Referring to FIGS. 1, 3, and 4, an upper part of a body 2 of the syringe drive device 1 is provided with a cylinder holding section 3 which detachably holds the cylinder 201, and a piston manipulating section 4 detachably engaged with the jaw portion 202a of the piston 202 behind the cylinder holding section 3. The body 2 is provided with a piston drive section 5 which moves the piston manipulating section 4 to thereby move the piston 202 in a direction where the piston is pushed into or pulled out from the cylinder 201. The body 2 further includes a pair of left and right rear cover portions 2a and 2b on the rear side thereof, and a front cover portion 2c extending forward from the cylinder holding section 3.

A grip portion 2d which can be gripped by an operator with one hand is provided on the lower side of the body 2 of the syringe drive device 1. The grip portion 2d extends in a direction substantially orthogonal to the longitudinal direction of the cylinder 201 held by the cylinder holding section 3. Operation buttons 6A and 6B are provided on the front side of the grip portion 2d. The operator holds the grip portion 2d with his hand in manner of grasping a gun. Then, the operator presses the operation button 6A, 6B with his forefinger while locating all of his fingers except the forefinger on a finger location face 2e which is the front face of the grip portion 2d in manner of pulling the trigger.

Referring to FIGS. 1, 3, and 4, a recessed section 11 fittable to the outer shape of the cylinder 201 of the syringe 200A is formed in the upper face of the cylinder holding section 3. The cylinder holding section 3 further has a groove 12 into which the flange portion 201b of the cylinder 201 is inserted, and a seizing piece 13 provided at a position ahead of the groove 12. The groove 12 secures a position of the cylinder 201 in the direction of central axis. The seizing piece 13 can rotate to and from a closing position illustrated in FIG. 1 and an open position illustrated in FIG. 3. When engaged with a locking claw 14 at the closing position, the seizing piece 13 is held with pushing the cylinder 201. When the seizing piece 13 is disengaged from the locking claw 14 to rotate to the open position, the cylinder 201 can be removed from the cylinder holding section 3.

A rotation shaft 15, which is the center of rotation, is provided on one end side of the seizing piece 13. A spring (not illustrated in the drawings) attached to a lower part of the rotation shaft 15 elastically energizes the seizing piece 13 downward. When the free other end of the seizing piece 13 is raised against the energizing force, the seizing piece 13 can be rotated between the closing position and the open position. The engagement with the locking claw 14 prevents the cylinder 201 secured to the seizing piece 13 from accidentally falling off. To make it easier to pinch the locking claw 14 for making the operation easy, a part of the locking claw 14 protrudes to a height larger than the seizing piece 13.

Referring to FIGS. 1, 3, and 4, the piston manipulating section 4 has a groove 21 into which the jaw portion 202a of the piston 202 provided in the syringe 200A is inserted. The piston manipulating section 4 has a coupling piece 22 rotatable to and from a closing position illustrated in FIG. 1 and an open position illustrated in FIG. 3 at a position ahead of the groove 21. When the coupling piece 22 at the closing position is engaged with a locking claw 23 while the jaw portion 202a of the piston 202 is still inserted in the groove 21, the jaw portion 202a thereby nipped between the coupling piece 22 and the groove wall of the groove 21 can be secured to the piston manipulating section 4, so that the piston 202 is coupled with the piston manipulating section 4. When the coupling piece 22 is disengaged from the locking claw 23 to rotate to the open position, the jaw portion 202a can be removed from the groove 21 to decouple a connection between the piston 202 and the piston manipulating section.

A rotation shaft 24, which is the center of rotation, is provided on one end side of the coupling piece 22, and a spring (not illustrated in the drawings) attached to a lower part of the rotation shaft 24 elastically energizes the coupling piece 22 downward. When the free other end of the coupling piece 22 is raised against the energizing force, the coupling piece 22 can be rotated between the closing position and the open position. The engagement with the locking claw 23 prevents the jaw portion 202a secured to the coupling piece 22 from accidentally falling off. To make it easier to pinch the locking claw 23 for making the operation easy, a part of the locking claw 23 protrudes to a height larger than the coupling piece 22.

Figure 5:
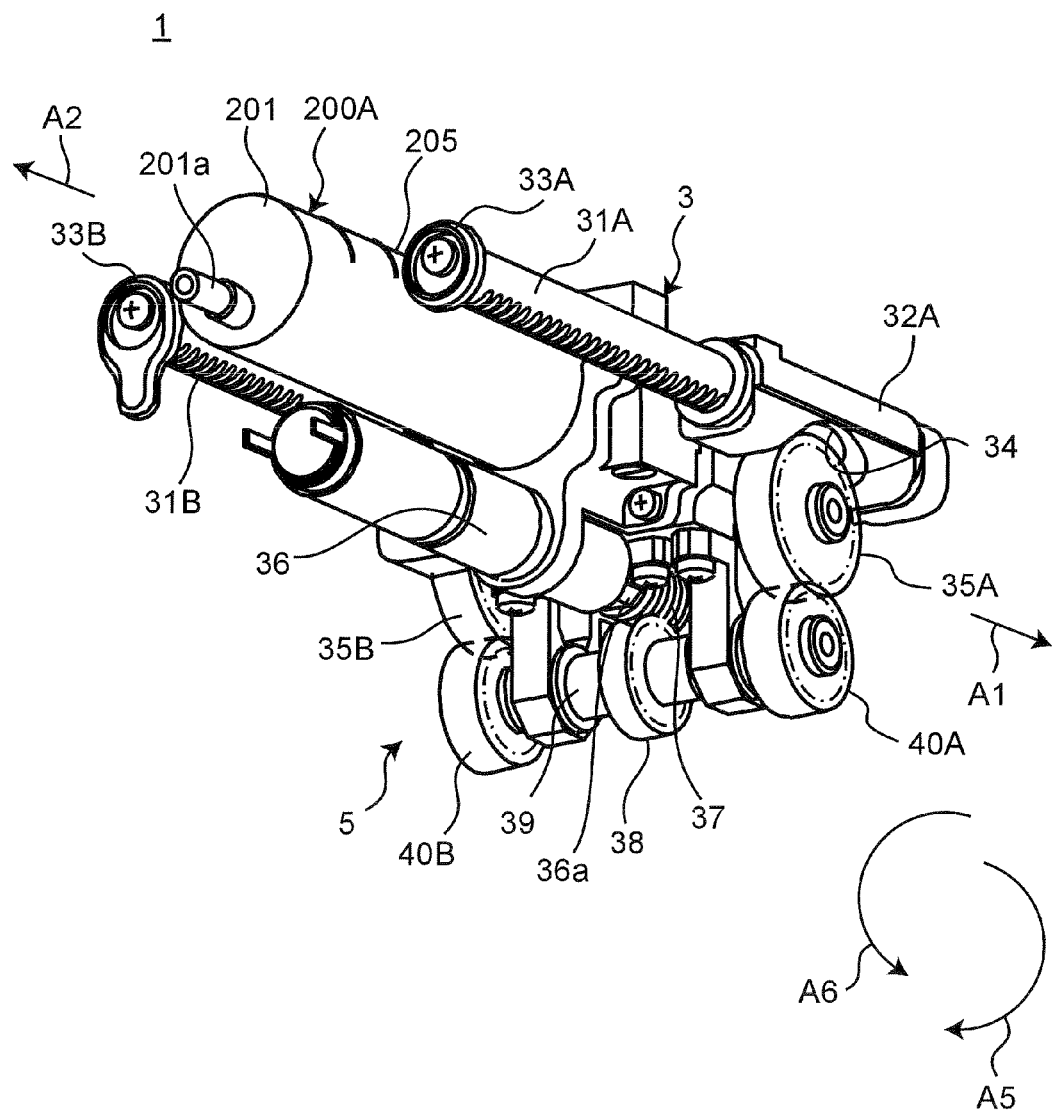
FIG. 5 is a perspective view of a piston drive section according to the embodiment 1 from below.
Figure 6:
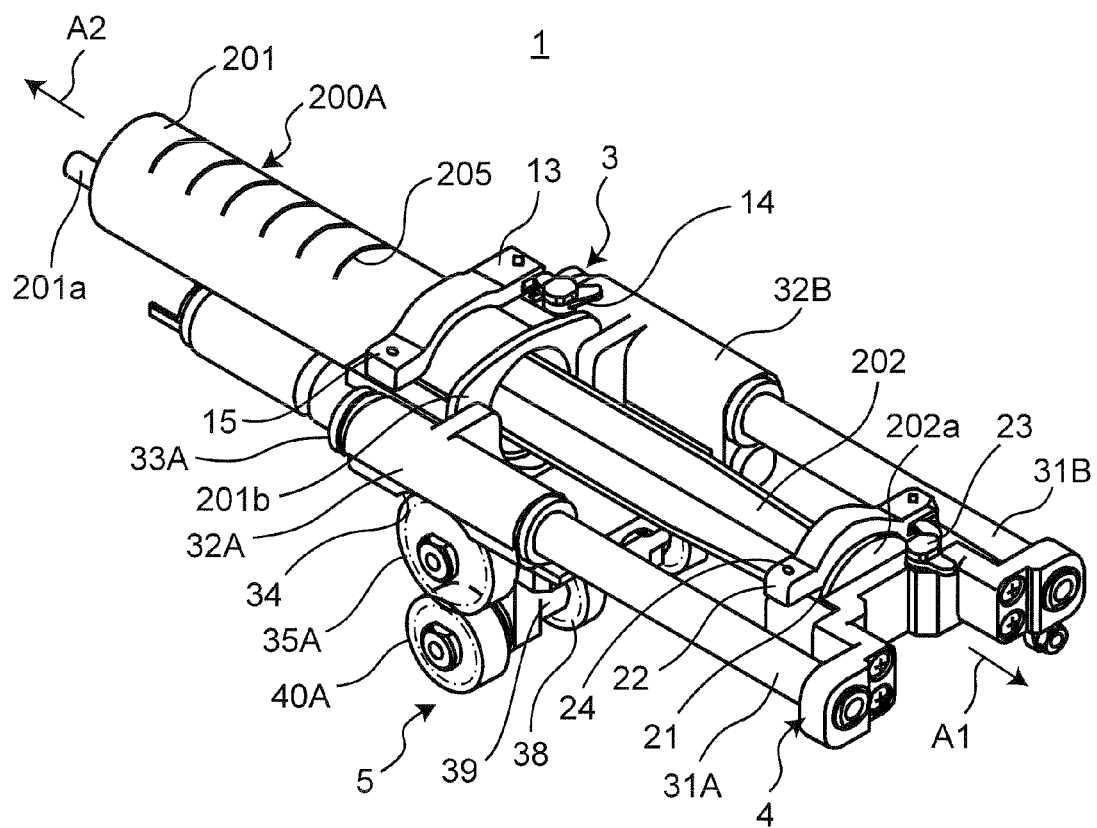
FIG. 6 is a perspective view of the piston drive section according to the embodiment 1 from above.

FIGS. 5 and 6 illustrate the piston drive section 5 after the body 2 is removed from the syringe drive device 1, along with a piston manipulating section 4, a syringe 200A, and a cylinder holding section 3. The piston drive section 5 has a pair of racks (driving members) 31A and 31B provided on both sides of the cylinder 201. The pair of racks 31A and 31B according to the present embodiment are straight cylindrical rods having lower faces notched at intervals. The racks 31A and 31B are situated so as to extend in parallel with the central axis of the piston 202. The racks 31A and 31B are supported by cylindrical bearings 32A and 32B respectively having open ends on both sides thereof so as to linearly move in parallel with the central axis of the piston 202. The rear ends of the racks 31A and 31B are coupled with protruding portions of the piston manipulating section 4 on left and right sides thereof. The positions at which the racks 31A and 31B are coupled with the piston manipulating section 4 are bilaterally symmetric to the center axis of the piston 202. The rear end of the piston manipulating section 4 is attached with a rack end cover 41. A moving limit of the racks 31a and 31b in a forward direction is regulated by a close contact of the piston manipulating section 4 with the bearings 32A and 32B. A moving limit of the racks 31a and 31b in a backward direction is regulated by a close contact of fall-off preventing members 33A and 33B provided at ends of the racks 31A and 31B with the bearings 32A and 32B.

The racks 31A and 31B are engaged with gears 35A and 35B via dented portions 34 provided on lower parts of the bearings 32A and 32B. A rotation force is transmitted from a motor 36, which is a power source, to the gears 35A and 35B. The motor 36 is situated so that an output shaft 36a thereof is in parallel with the central axis of the piston 202. The rotation of the motor 36 is transmitted from a warm gear 37 secured to the output shaft 36a to a gear 38, and then transmitted to the gears 35A and 35B by way of gears 40A and 40B on left and right secured to a common shaft 39 with the gear 38. The rotation of the gears 35A and 35B makes the racks 31A and 31B linearly move. When the racks 31A and 31B move, the piston 202 coupled with the racks 31A and 31B by way of the piston manipulating section 4 moves in a direction where the piston is pushed into or pulled out from the cylinder 201.

According to the present embodiment, the motor 36 is reversely rotated when the operation button 6A is pressed. When the motor 36 reversely rotates, the gears 35A and 35B rotate clockwise (direction illustrated with arrow A5) on the drawings of FIGS. 5 and 6, and the racks 31A and 31B move the piston manipulating section 4 in the direction where the piston 202 is pulled out from the cylinder 201 as illustrated with arrow A1. On the other hand, the motor 36 is normally rotated when the operation button 6B is pressed. When the motor 36 normally rotates, the gears 35A and 35B rotate anticlockwise (direction illustrated with arrow A6) on the drawings of FIGS. 5 and 6, and the racks 31A and 31B move the piston manipulating section 4 in the direction where the piston 202 is pushed into the cylinder 201 as illustrated with arrow A2.

The rotation of the motor 36 is transmitted from the warm gear 37 to the racks 31A and 31B by way of the bilaterally symmetric gears 40A and 40B and gears 35A and 35B. The racks 31A and 31B are coupled with the piston manipulating section 4 at positions bilaterally symmetric to the center axis of the piston 202. Thus, the piston drive section 5 is configured as a driving force transmission mechanism wherein the structural elements are substantially bilaterally symmetric to the center axis of the piston 202. This structural characteristic serves to cancel a moment load acting on the piston manipulating section 4 and the piston drive section 5 when the piston 202 is driven, making it unnecessary that the piston manipulating section 4 and the piston drive section 5 be strong enough against such a large moment load. Therefore, aluminum rods having a small diameter, for example, can be used as the racks 31A and 31B on left and right. The gears 35A, 35B, 38, 40A, and 40B may be made of synthetic resin. Thus, the piston manipulating section 4 and the piston drive section 5 can be downsized, consequently reducing the whole structure of the syringe drive device 1 in size and weight. As a result of such a reduction in size and weight, the syringe drive device 1 according to the present embodiment can be provided as a mobile device that can be easily held and used with one hand as described so far. Therefore, a medication dispensing operation using the syringe drive device 1 according to the present embodiment can be easily performed in any suitable place other than a dispensing room (for example, nurse station). The syringe drive device achieves a high efficiency in the dispensing operation.

When the syringe drive device 1 is used, the syringe drive device 1 loaded with the syringe 200A is held with one hand, and the injection needle 203 is punctured into a rubber cap of a medicinal solution container held with the other hand such as vial container or infusion bag. After the injection needle 203 is thus punctured into the rubber cap, the syringe 200A and the medicinal solution container form an enclosed space with no leak of air therefrom. When the operator presses the operation button 6A with the forefinger of his hand grasping the grip portion 2d in manner of grasping a gun, the piston 202 is moved in the direction where the piston is pulled out from the cylinder 201 alongside the piston manipulating section 4 as illustrated with arrow A1, and a medicinal solution or air in the medicinal solution container is suctioned into the syringe 200A. When the operation button 6B is pressed, the piston 202 is moved in the direction where the piston is pushed into the cylinder 201 alongside the piston manipulating section 4 as illustrated with arrow A2, and the medicinal solution or air in the syringe 200A is injected into the medicinal solution container. There is no movement of the piton manipulating section 4 or the piston 202 unless the operation button 6A or 6B is pressed. As described so far, the syringe drive device 1 according to the present embodiment can easily suction or inject the medicinal solution to and from the syringe 200A when the operator simply presses the operation button 6A, 6B while holding the syringe drive device 1 loaded with the syringe 200A with one hand and the medicinal solution container with the other hand.

Next is described the syringe drive device 1 according to the present embodiment that can be loaded with the large syringe 200A and the small syringe 200C both.

Figure 7:
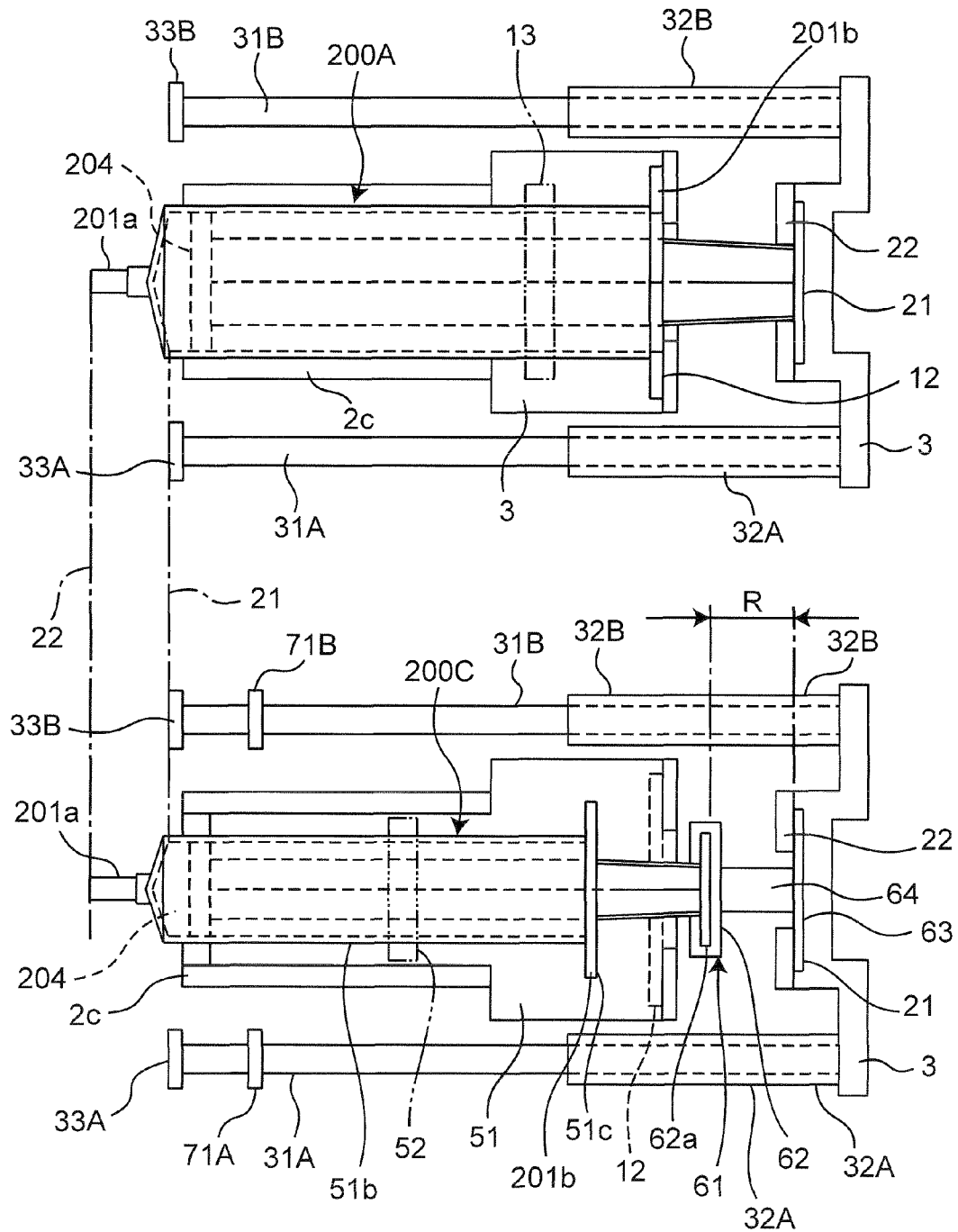
FIG. 7 is a schematic plan view comparatively illustrating the syringe drive device where the adapter is used and the syringe drive device where no adapter is used according to the embodiment 1.
Figure 8:
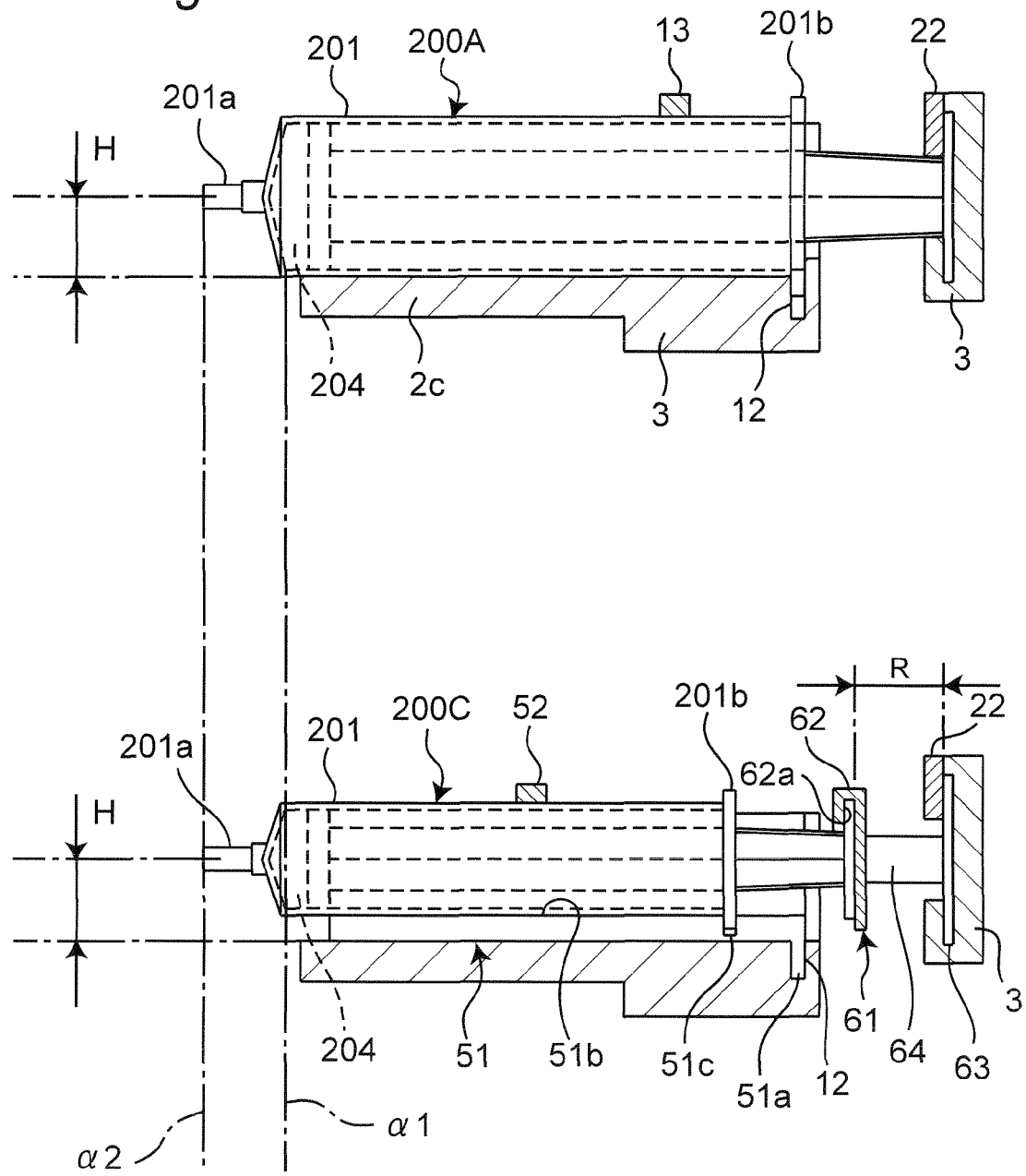
FIG. 8 is a schematic longitudinal view in section comparatively illustrating the syringe drive device where the adapter is used and the syringe drive device where no adapter is used according to the embodiment 1.

When the large syringe 200A is loaded in the syringe drive device 1, the cylinder 201 of the syringe 200A is directly coupled with the cylinder holding section 3, and the jaw portion 202a of the piston 202 is directly coupled with the piston manipulating section 4. As illustrated in FIGS. 2, 7, and 8, when the small syringe 200C is loaded in the syringe drive device 1, the cylinder 201 is loaded in the cylinder holding section 3 by means of the cylinder adapter 51, and the piston 202 is coupled with the piston manipulating section 4 by means of the piston adapter 61.

Referring to FIGS. 7 and 8, the lower face of the cylinder adapter 51 is placed on upper faces of the cylinder holding section 3 and the front cover portion 2c of the body 2. An engaging piece 51a protruding downward is provided on the lower face of the cylinder adapter 51 on the rear end side thereof. When the engaging piece 51a is pushed into the groove 12, the cylinder adapter 51 is positionally fixed in the direction of central axis of the piston 202. A locking mechanism (not illustrated in the drawings) is provided to secure and release the cylinder adapter 51 to and from the cylinder holding section 3 or the front cover portion 2c. A recessed portion 51b fittable to the outer shape of the cylinder 201 provided in the syringe 200C is formed in the upper face of the cylinder adapter 51. A groove 51c is formed in the recessed portion 51b. When the flange portion 201b is pushed into the groove 51c, the cylinder 201 is positionally fixed relative to the cylinder adapter 51 (in the direction of central axis of the piston 202). The cylinder adapter 51 has a seizing piece 52 used to detachably hold the cylinder 201 housed in the recessed portion 51b. The seizing piece 52 has a structure and a function similar to those of the seizing piece 13 of the cylinder holding section 3. The seizing piece 52 can rotate to and from a closing position and an open position. When the seizing piece 52 at the closing position is engaged with a locking claw not illustrated in the drawings, the seizing piece 52 is held with pushing the cylinder 201. When the seizing piece 52 is disengaged from the locking claw to rotate to the open position, the cylinder 201 can be removed from the cylinder adapter 51.

The shape and dimension of the cylinder adapter 51 according to the present embodiment are designed so that the position of the cylinder 201 in the direction of central axis of the piston 202 is equally retained whether the large syringe 200A is directly loaded in the syringe drive device 1 or the small syringe 202C is loaded in the syringe drive device 1 by means of the cylinder adapter 51. This point is described below.

Referring to FIG. 1, when the large syringe 200A is loaded, the end of the cylinder 201 protrudes farther than a reference face 2f (at a given position away from the finger location face 2e) which is the front end face of the body 2 (front cover portion 2c) according to the present embodiment. More specifically, as illustrated with a reference symbol α1 in FIGS. 7 and 8, the position of the cylinder 201 is set so that the position of the gasket 204 (initial reference position) when the piston 202 is pushed into the cylinder 201 to the far end (initial position) corresponds to the ends of the racks 31A and 31B at the most forward position thereof (to be more precise, front end faces of the fall-off preventing members 33A and 33B provided in the ends of the racks 31A and 31B). As illustrated with the reference symbol α1 in FIGS. 7 and 8, when the cylinder adapter 51 is used to load the small syringe 200C in the syringe drive device 1, the position of the cylinder 201 is set so that the initial reference position of the gasket 204 corresponds to the ends of the racks 31A and 31B at the most forward position thereof. As illustrated with a reference symbol α2 in FIGS. 7 and 8, whichever of the syringes 200A and 200C is loaded in the syringe drive device 1, the end of the cylinder 201 (tip of the solution port 201a) in the axial direction of the piston 202 is equally positioned.

According to the present embodiment, whichever of the syringes 200A and 200C having different storage capacities is loaded, the position of the cylinder 201 (position in the axial direction of the piston 202) is equally set. Therefore, a length L1 from the reference face 2f to the tip of the injection needle 203 stays substantially equal because, as shown in FIG. 8, a tip end side of the syringes 200A and 200B will be located at the same position. When the medicinal solution is suctioned from the medicinal solution container such as vial container or injected into the container such as infusion bag, the operator can handle any syringes regardless of their storage capacities. Such a syringe drive device can improve the workability.

Whichever of the syringes 200A and 200C with different storage capacities is loaded in the syringe drive device 1, the initial reference position of the gasket 204 corresponds to the ends of the racks 31A and 31B at the most forward position thereof. Therefore, the scale marks 205 of the cylinder 201 are unlikely to be blocked by the racks 31A and 31B. Specifically, when the operation button 6B is pressed to move the piston 202 in the push-in direction or pull-out direction, the racks 31A and 31B move with the gasket 204 in the push-in direction or pull-out direction, and the positions of the gasket 204 and the racks 31A and 31B (positions in the direction of central axis of the piston 202) always remain unchanged. Whichever of the syringes 200A and 200C respectively having different storage capacities is loaded, the scale marks 205 of the cylinder 201 can be easily read, which helps the working steps to be accurately and easily performed. Whichever of the syringes 200A and 200C respectively having different storage capacities is loaded, the ends of the racks 31A and 31B always correspond to the position of the gasket 204. Therefore, the liquid surface of the medicinal solution in the cylinder 201 is not blocked by the racks 31A and 31B but can be reliably read.

Depending on an angle at which the scale marks 205 are read, the ends of the racks 31A and 31B possibly overlap with the gasket 204, making it a little difficult to read the scale marks 205. In such an event, a position where the ends of the racks 31A and 31B are on the scale marks 205 is checked, so that the positions on the scale marks 205 of the gasket 204 are indirectly read. When, for example, scale marks are provided on the side faces of the racks 31A and 31B on the opposite side of the cylinder 201, the scale marks in the parts of the racks 31A and 31B drawn into the front end faces of the bearings 32A and 32B can be read to indirectly confirm the position of the gasket 204 on the scale marks 205.

As described above, whichever of the syringes 200A and 200C respectively having different storage capacities is, the initial reference position of the gasket 204 corresponds to the ends of the racks 31A and 31B at the most forward position thereof (positions in the direction of central axis of the piston 202). Therefore, the tip of the injection needle 203 stays at the same position, and the scale marks 205 can be easily read. This improves the workability, helping to reliably inject and mix the medicinal solution to be contained in, for example, an infusion bag. When the initial reference position of the gasket 204 and the positions of the ends of the racks 31A and 31B at the most forward position thereof are thus set, the syringe drive device 1 can be further downsized in the direction of central axis of the piston 202.

An alternative proposal for the position setting in the syringes 200A and 200C (in the direction of central axis of the piston 202) is to set the initial reference position of the gasket 204 at the constant position behind the ends of the racks 31A and 31B at the most forward position thereof, whichever of the syringes 200A and 200C respectively having different storage capacities is used. This structural characteristic makes it even more unlikely that the gasket 204 is blocked by the ends of the racks 31A and 31B, so that the scale marks 205 of the cylinder 201 can be more easily read. This improves the workability, helping to reliably inject and mix the medicinal solution to be contained in, for example, infusion bag. It is desirably avoided to set the initial reference position of the gasket 204 behind the ends of the racks 31A and 31B at the most forward position thereof. This is because it makes it difficult to read the scale marks 205 at the position of the gasket 204 which are blocked by the racks 31A and 31B.

The shape and dimension of the cylinder adapter 51 according to the present embodiment are designed so that the height position of the solution port 201a measured from the outer periphery of the cylinder 201 is equally retained regardless of whether the large syringe 200A is directly loaded in the syringe drive device 1 or the small syringe 200C is loaded in the syringe drive device 1 by means of the cylinder adapter 51. This point is described below.

As illustrated in FIG. 1, the upper face portion of the cylinder 201 of the large syringe 200A directly loaded in the cylinder holding section 3 where the scale marks 205 are provided is above a virtual plane P1 including the central axes of the racks 31A and 31B. Therefore, the scale marks 205 and the volume of medicinal solution in the cylinder 201 can be read without being hidden by the racks 31A and 31B when the medicinal solution is injected or pushed out, which helps the operator to steadily perform the working steps. As illustrated with a reference symbol H in FIG. 8, when the cylinder 201 of the small syringe 200C is loaded in the cylinder holding section 3 by means of the cylinder adapter 51, a height dimension from the upper faces of the front cover portion 2c of the body 2 and the cylinder holding section 3c to the solution port 201a is equal to a height dimension of the same when the cylinder 201 of the large syringe 200A is directly loaded in the cylinder holding section 3. Therefore, when the small syringe 200C is loaded, the upper face portion of the cylinder 201 provided with the scale marks 205 is above the virtual plane P1 as illustrated in FIG. 2, preventing the racks 31A and 31B from blocking the scale marks 205. Therefore, the scale marks 205 can be unfailingly read.

Next, the piston adapter 61 is described. When the cylinder adapter 51 is used to load the small syringe 200C in the syringe drive device 1, the position of the cylinder 201 (position in the direction of central axis of the piston 202) remains unchanged whichever of the syringes 200A and 200C respectively having different storage capacities is used. As illustrated with a reference symbol R in FIGS. 7 and 8, when the small syringe 200C is loaded in the syringe drive device 1, there is a gap between the jaw portion 202a of the piston 202 and the piston manipulating section 4. In this case, it is not possible to directly couple the jaw portion 202a of the piston 202 with the piston manipulating section 4. Therefore, when the small syringe 200C is loaded in the syringe drive device 1, the jaw portion 202a of the piston 202 is coupled with the piston manipulating section 4 by means of the piston adapter 61.

The piston adapter 61 has a front-side coupling section 62 provided with a groove 62a into which the jaw portion 202a of the piston 202 is detachably housed, and a rear-side coupling section 63 having a plate shape and housed in the groove 21 to be detachably coupled with the piston manipulating section 4 by the coupling piece 22. The front-side coupling section 62 and the rear-side coupling section 63 are coupled with each other by a rod-shape section 64. As the piston manipulating section 4 moves, the piston 202 coupled there-with by means of the piston adapter 61 thereby moves in the push-in direction or the pull-out direction relative to the cylinder 201.

As far as the piston 202 of the small syringe 200C loaded by means of the cylinder adapter 51 can be detachably coupled with the piston manipulating section 604, and the piston adapter 61 has an enough strength subject to the driving force transmitted from the piston manipulating section 4, specific structural of the piston adapter 61 are not particularly limited.

As is clearly known from FIGS. 7 and 8, a movable range requested for the piston 202 of the syringe drive device 1 loaded with the small syringe 200C is smaller than that of the syringe drive device 1 loaded with the large syringe 200A. Therefore, the piston 202 of the syringe drive device 1 loaded with the small syringe 200C possibly falls off from the cylinder 201 in the case where the racks 31A and 31B are driven in the movable range set in the device loaded with the large syringe 200A. Therefore, in the present embodiment, fall-off preventing pieces 71A and 71B are detachably attached at positions behind the fall-off preventing members 33A and 33B of the racks 33A and 33B when the small syringe 200C is used. These fall-off preventing members 71A and 71B restrict a range of reciprocating movement of the racks 31A and 31B so that the piston 202 does not fall off from the cylinder 201.

The syringe drive device 1 according to the present embodiment, which is designed as a mobile device that can be held and used with one hand, is also designed to ensure the operator's safety. This point is described below.

Referring to FIGS. 1 to 4, the rear cover portions 2a and 2b protruding outward are provided on the both sides of the cylinder holding section 3 above the grip portion 2d of the body 2, and teeth of the racks 31A and 31B exposed from bored portions 34 of the bearings 32A and 32B and the gears 35A, 35B, 38, 40A, and 40B are housed in the rear cover portions 2a and 2b. This structural characteristic prevents the operator's hand grasping the grip portion 2d from touching the teeth of the racks 31A and 31B, and the gears 35A, 35B, 38, 40A, and 40B. Because the rear cover portions 2a and 2b have such a shape that protrudes from either side of the cylinder holding section 3, the rear cover portions 2a and 2b prevent the thumb and forefinger of the operator's hand grasping the grip portion 2d from touching the teeth of the racks 31A and 31B exposed from the bored portions 34 on the lower side of the bearings 32A and 32B, and the gears 35A and 35B meshed with the teeth. The motor 36 and the warm gear 37 are stored in the body 2 as well. Thus, the syringe drive device 1 ensures the operator's safety. According to the embodiment 1, the body 2 including the rear cover portions 2a and 2b and the front cover portion 2c is formed as a unit so that number of device parts is not increased. Therefore, the syringe drive device 1 can be reduced in size and weight.

The rack end cover 41 attached to the rear end of the piston manipulating section 3 coupled with the racks 31A and 31B has a curved rear face protruding in an arc shape. Because of the curved rear face, when the syringe drive device 1 is put on, for example, a desk with the end of the syringe 200A directed upward, the syringe drive device 1 is rotated to right or left so that the syringe 200A lies on its side. This avoids such an incident that the syringe drive device 1 is placed on, for example, a desk with the injection needle 203 attached to the solution outlet 201a directed upward. The syringe drive device 1 is thus structurally designed with great cares to ensure the operator's safety during use. According to the present embodiment, the rack end cover 41 is formed separately from the piston manipulating section 4, however, these members may be integrally formed.

According to the embodiment 1, the piston 202 is driven in the direction where the medicinal solution is suctioned into the cylinder 201 when the operation button 6A is pressed but is driven in the direction where the medicinal solution is pushed out from the cylinder 201 when the operation button 6B is pressed. The operation buttons 6A and 6B may be formed in different shapes so that the operator can instantly know which of the operation buttons 6A and 6B the operator is touching with the finger when the operator touches the button. For example, the operation button 6A has a protruding head, while the operation button 6B has a dented head, or one of the operation buttons 6A and 6B may be larger in height than the other. These suggested structural differences can exert a similar effect. The operation button 6B, in particular, is pressed to drive the piston in the direction where the medicinal solution is pushed out from the cylinder 201. Any wrong operation is desirably avoided to minimize the risk of leaking the medicinal solution. Therefore, the operation button 6B is desirably formed in a distinguishable shape, for example, larger or lower height than the operation button 6A, to forewarn the operator. Another suggestion is to separately provide an enable button (not illustrated in the drawings), wherein the operator has to press the enable button and the operation button 6B both at the same time in order to drive the piston 202 in the direction where the medicinal solution is pushed out from the cylinder 201.

FIG. 9 illustrates a modified embodiment of the syringe drive device 1 according to the embodiment 1. When the medicinal solution is suctioned from the medicinal solution container into the cylinder 201, air is possibly suctioned with the medicinal solution into the cylinder 201, in which case it is necessary to remove the air from the cylinder 201 before suctioning a next medicinal solution or injecting the suctioned medicinal solution into a container such as infusion bag. The modified embodiment of the embodiment 1 facilitates the removal of air.

As is clear from the illustration of FIG. 9, the solution port 201a formed in one end of the cylinder 201 is provided at an eccentric position from its central axis. When the medicinal solution is suctioned from the medicinal solution container into the cylinder 201, the cylinder 201 is situated with the solution port 201a below its center as illustrated in FIG. 1. The volume of the medicinal solution to be suctioned is adjusted referring to the scale marks 205 on the upper face of the cylinder 201 thus situated. When the piston 202 is moved in the push-in direction (direction illustrated with arrow A2) for the removal of air while the cylinder 201 is situated so that the solution port 201a is below its center as illustrated in FIG. 1, the medicinal solution flows out from the cylinder 201 before the removal of air. Therefore, it is necessary to rotate the cylinder 201 through 180 degrees on its central axis before moving the piston 202 in the push-in direction for the removal of air so that the solution port 201a is above the center as illustrated with broken lines in FIG. 9.

As illustrated in FIG. 9, for example, rotatable rollers 72A and 72B are provided at two circumferential positions on right and left in lower parts of the cylinder holding section 3, and a rotatable roller 73 is provided on the lower face of the seizing piece 13. In the cylinder holding section 3, the outer periphery of the cylinder 201 is retained by the rollers 72A, 72B, and 73 at three positions rotatably around an axial line thereof. Therefore, the cylinder 201 can be rotated through 180 degrees on its center axis without disengaging the cylinder 201 from the seizing piece 13, so that the solution port 201a can be easily relocated above the center. Thus, the preparatory step (rotation of the cylinder 201) before the removal of air can be easily performed, which improves the workability.

When the piston 202 is moved in the push-in direction after the cylinder 201 is situated so that the solution port 201a is above the center, the air in an upper part of the cylinder 201 smoothly flows out through the solution port 201a. The medicinal solution staying in a lower part of the cylinder 201 is always below the air due to its own weight, preventing the medicinal solution from accidentally flowing out from the cylinder 201.

To return the cylinder 201 so that the solution port 201a is at a position below the center illustrated with a solid line in FIG. 9, the cylinder 201 can be easily rotated around its own axial line without disengaging the cylinder 201 from the seizing piece 13, which improves the workability.

When the cylinder 201 is rotated on its central axis, the flange portion 201b on the rear end thereof is rotated in the groove 12 of the cylinder holding section 3. The modified embodiment of FIG. 9, therefore, makes it necessary to form the groove 12 to have a depth dimension adequately larger than the largest width of the flange portion 201b so that the rotation of the flange portion 201b is not disturbed.

It is desirable to couple the jaw portion 202a of the piston 202 with the piston manipulating section 4 using the coupling piece 22 such that the piston 202 is rotatable on its own central axis. Thus, the piston 202 rotate substantially integral with the rotating cylinder 201, thereby preventing the inner face of the cylinder 201 from sliding with the outer peripheral face of the gasket 204 due to relative rotation of the cylinder 201 and the piston 202.

[Embodiment 2]

Figure 12:
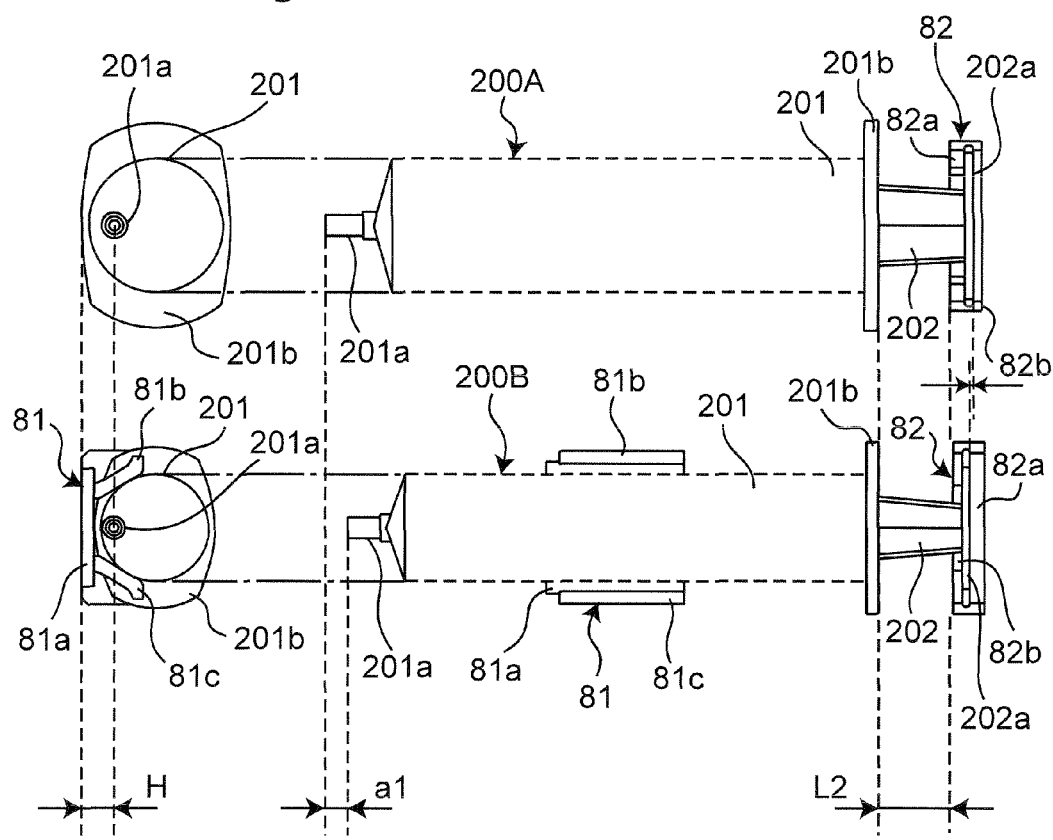
FIG. 12 is a plan view and a front view comparatively illustrating the syringes respectively having the storage capacities of 50 cc and 30 cc loaded in the syringe drive device according to the embodiment 2.

FIGS. 10 to 12 illustrate a syringe drive device 1 according to an embodiment 2 of the present invention. In the syringe drive device 1 according to the present embodiment, any of the large syringe 200A and the intermediate syringe 200B among the syringes illustrated in FIG. 14 with different storage capacities can be loaded and used without replacing any device components. As illustrated in FIG. 11A, a piston adapter 82 alone is used when the large syringe 200A is loaded in the syringe drive device 1. As illustrated in FIG. 11B, a cylinder adapter 81 and the piston adapter 82 are both used when the intermediate syringe 200B is loaded in the syringe drive device 1.

As illustrated with a reference symbol α1 in FIGS. 12 and 14, there is only a relatively small difference between distances from the flange portions 201b of the respective cylinders 201 to the ends (ends of the respective solution ports 201a) in the large syringe 200A and the intermediate syringe 200B. Therefore, the position of the tip of the injection needle 203 does not largely change between the syringes 200A and 200B without the positional adjustment in the direction of central axis of the piston 202 using the cylinder adapter 81. As a result, the usability felt by the operator is substantially the same. Different to the cylinder adapter 51 according to the embodiment 1, the cylinder adapter 81 used in the syringe drive device 1 according to the present embodiment only serves to equally retain the height position of the solution port 201a between the syringe drive devices 200A and 200B as illustrated with a reference symbol H in FIG. 12.

As illustrated in FIGS. 10, 11B, and 12, the cylinder adapter 81 has a base portion 81a detachably secured to the front cover portion 2c of the body 2, and supporting pieces 81b and 81c extending obliquely upward from the base portion 81a to support the lower face side of the cylinder 201 of the syringe 200B. The cylinder adapter 81 thus interposed between the cylinder 201 and the front cover portion 2c increases the height dimension of the cylinder 201 of the syringe 200B. When the cylinder adapter 81 is thus used, the solution port 201a of the cylinder 201 of the intermediate syringe 200B held by the cylinder holding section 3 has a height position equal to that of the solution port 201a of the cylinder 201 of the large syringe 200A directly loaded in the cylinder holding section 3. As far as the height positions of the solution ports 201a of the both devices are equally set, specific structural of the cylinder adapter 81 are not particularly limited.

As illustrated with a reference symbol δ in FIG. 12, there is a relatively small difference between the positions of the respective jaw portions 202a (in the direction of central axis of the piston 202) in the syringes 200A and 200B when the respective pistons 202 are pushed into the cylinders 201 to the far end (initial positions). The difference δ, however, directly affects the accuracy of the medicinal solution volumes to be respectively suctioned and injected in the syringes 200A and 200B. Therefore, the present embodiment cancels the difference δ by using the cylinder adapter 81.

As is expressly illustrated in FIG. 10, a recessed housing section 83 having an open upper end is formed in the piston manipulating section 4 according to the present embodiment. The piston adapter 82 can be housed in and removed from the recessed housing section 83. The piston adapter 82 housed in the recessed housing section 83 is positionally fixed in the direction of central axis of the piston 202 when the outer sides of wall portions 82a and 82b in the longitudinal direction thereof abut the inner wall of the recessed housing section 83. The wall portions 82a and 82b of the piston adapter 82 face each other with an interval therebetween, the interval being equal to or slightly larger than the thickness of the jaw portion 202a of the piston 202. The interval constitutes a groove 84 in which the jaw portion 202a of the piston 202 is housed and held. A thickness t1 of the wall portion 82a is larger than a thickness of t2 of the other wall portion 82b. The wall portions 82a and 82b are respectively provided with cutout portions 82c and 82d having an arc shape to let the piston 202 pass therethrough.

As illustrated in FIG. 11A, when the large syringe 200A is loaded, the jaw portion 202a of the piston 202 is housed in the groove 84 of the piston adapter 82 which is situated so that the cutout portion 82c is directed upward and the wall portion 82a is directed forward. As illustrated in FIG. 11B, when the intermediate syringe 200B is loaded, the jaw portion 202a of the piston 202 is housed in the groove 84 of the piston adapter 82 which is situated so that the cutout portion 82d is directed upward and the wall portion 82b is directed forward. When the piston adapter 82 is thus loaded to the piston 202 with the wall portions 82a and 82b positionally reversed, there is an equal distance from the flange portion 201b of the cylinder 201 to the piston adapter 82 as illustrated with a reference symbol L2 in FIG. 12 between the syringe drive devices 200A and 200B. Therefore, the flange portion 201b of the cylinder 201 can be inserted in the groove 12, and the piston adapter 82 attached to the jaw portion 202a of the piston 202 can be housed in the recessed housing section 83 of the piston manipulating section 3 in the syringes 200A and 200B. According to the present embodiment, the reversible piston adapter 82 having a simple structure cancels any difference between the positions of the respective jaw portions 202a in the syringes 200A and 200B with different storage capacities, so that the piston is driven by the piston manipulating section 3.

[Embodiment 3]

Figure 13:
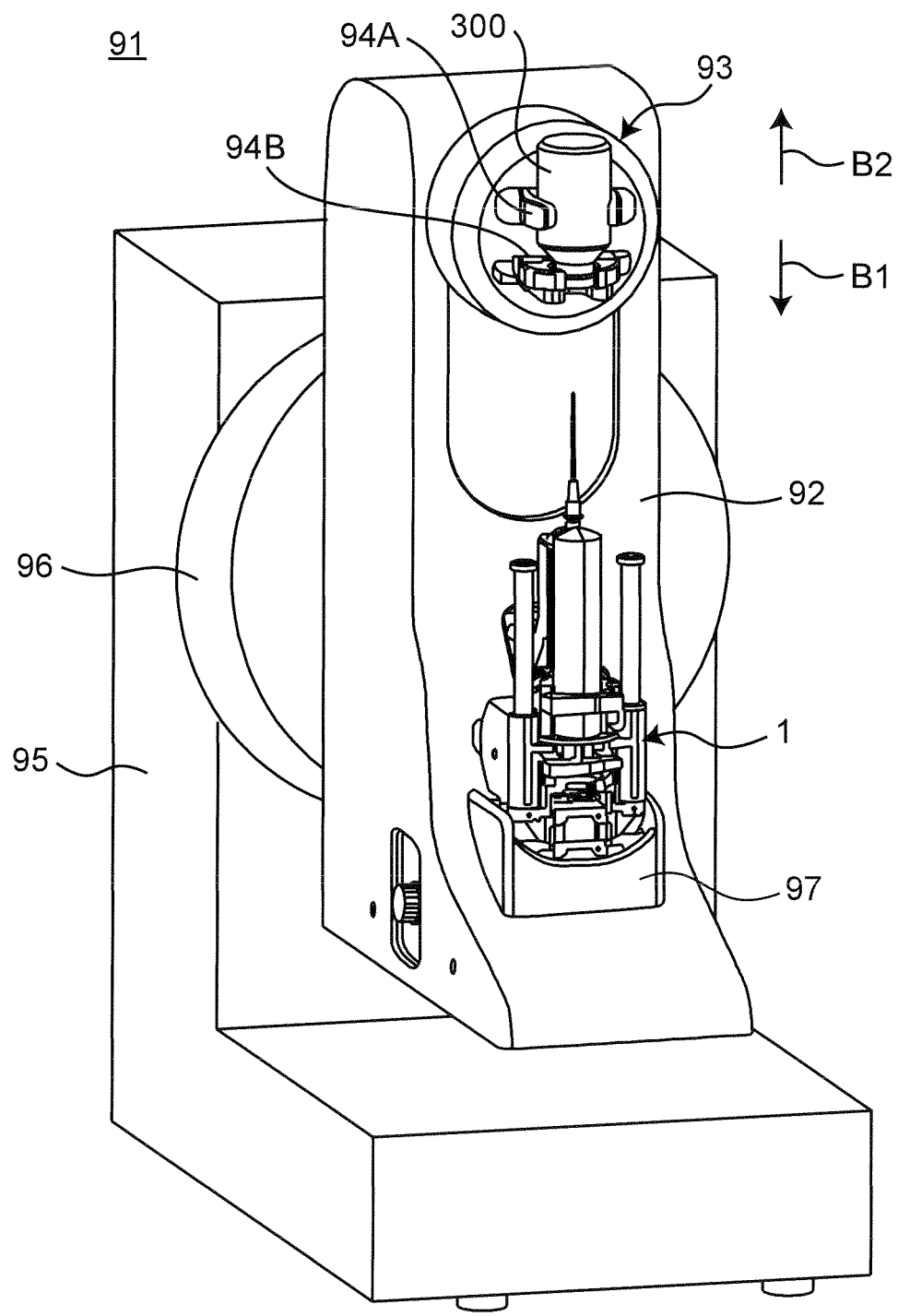
FIG. 13 is a perspective view of a medication dispensing apparatus device according to an embodiment 3 of the present invention.

FIG. 13 illustrates a medication dispensing apparatus device 91 to which the syringe drive device 1 according to the embodiment 1 is applied.

A movable section 92 of the medication dispensing apparatus device 91 has a syringe drive device holding section 97 which retains a syringe drive device 1 similar to the syringe drive device according to the embodiment 1 on one end side thereof, and a container holding section 93 on the other end side thereof. The container holding section 93 has openable and closable clamps 94A and 94B which detachably retain a medicinal solution container (vial container 300 in the present embodiment). The container holding section 93 linearly reciprocates on the movable section 92 in directions illustrated with arrows B1 and B2. When the container holding section 93 moves in the direction of arrow B1, the vial container 300 moves toward a syringe 200 loaded in the syringe drive device 1. When the container holding section 93 moves in the direction of arrow B2, the vial container 300 moves away from the cylinder 201. In place of moving the container holding section 93, the syringe drive device holding section 97 maybe configured to move toward and away from the container holding section 93, or the container holding section 93 and the syringe drive device 1 may both linearly reciprocate on the movable section 92.

The movable section 92 is coupled with a stationary pedestal section 95 at a position between the container holding section 93 and the syringe drive device holding section 97. A rotation drive section 96 is interposed between the movable section 92 and the pedestal section 95. As illustrated in FIG. 12, the rotation drive section 96 rotates the movable section 92 to take an upside-down position where the container holding section 93 is positioned on an upper side and the syringe drive device holding section 97 is on a lower side or a regular position opposite to the upside-down position where the syringe drive device holding section 97 is positioned on the lower side and the container holding section 93 is positioned on the upper side.

The medication dispensing apparatus device 91 can automatically suction and inject the medicinal solution to and from the syringe 200 and the vial container 300 by combining; shifting to and from the regular position and the upside-down position using the rotation drive section 96, moving the vial container 300 toward and away from the syringe 200 using the container holding section 93, and driving the syringe 200 using the syringe drive device 1. When the cylinder adapter 51 and the piston adapter 61 (for example, see FIGS. 7 and 8) are used, the syringe drive device 1 can be loaded with any of the syringes 200A and 200B respectively having different storage capacities in a manner similar to the embodiment 1. The present invention is not necessarily limited to a mobile syringe drive device but is also applicable to a desktop syringe drive device.

The present invention is not necessarily limited to the embodiments described so far but can be variously modified.

For example, the syringe drive device 1 according to the embodiment 1 may be provided with a volume adjusting section in the body 2. The volume adjusting section 2 is configured to adjust a driving speed or a driving force of the piston manipulating section 4 by the piston drive section 5 for the drive in the direction where the medicinal solution is suctioned into the cylinder 201 and the drive in the direction where the medicinal solution is pushed out from the cylinder 201. Particularly for the drive in the direction where the medicinal solution is suctioned into the cylinder 201, it is necessary to suction a given volume of medicinal solution, therefore, the driving force or the driving speed is desirably adjusted.

The piston drive section 5 according to the embodiment 1 transmits the output of the motor 36 to the shaft 39 using the warm gear 37 and the gear 38 to be distributed to the gears 40A and 40B, and then transmitted to the racks 31A and 31B by way of the gears 35A and 35B. The mechanism of the power transmission by the piston drive section 5 is not necessarily limited thereto. For example, bevel gears may be used as the warm gear 37 and the gear 38, or the gears 35A and 35B may be omitted so that the gears 40A and 40B having a large diameter are directly meshed with the racks 31A and 31B.

The present invention was described based on the examples where the cylinder shapes are variously different because of their different storage capacities. The present invention can be applied to syringes applicable to differently shaped cylinders manufactured by different manufacturers or according to different technical standards.

DESCRIPTION OF SYMBOLS 1 syringe drive device
2 body
2a, 2b rear cover portion
2c front cover portion
2d grip portion
2e finger location face
2f reference face
3 cylinder holding section
4 piston manipulating section
5 piston drive section
6A, 6B operation button
11 recessed portion
12 groove
13 seizing piece
14, 23 locking claw
15, 24 rotation shaft
21 groove
22 coupling piece
31A, 31B rack
32A, 32B bearing
33A, 33B fall-off preventing member
34 bored portion
35A, 35B, 38, 40A, 40B gear
36 motor
36a output shaft
37 warm gear
39 shaft
41 rack end cover
51, 81 cylinder adapter
51a engaging piece
51b recessed portion
51c groove
52 seizing piece
61, 82 piston adapter
62 front-side coupling section
62a groove
63 rear-side coupling section
64 rod-shape section
71A, 71B fall-off preventing member
72A, 72B, 73 roller
81a base portion
81b, 81c supporting piece
82a, 82b wall portion
82c, 82d cutout portion
83 recessed housing section 84 groove
91 medication dispensing apparatus
92 movable section
93 container holding section
94A, 94B clamp
95 pedestal section
96 rotation drive section
97 syringe drive device holding section
200A, 200B, 200C syringe
201 cylinder
201a solution port
201b flange portion
202 piston
202a jaw portion
203 injection needle
204 gasket
205 scale mark
300 vial container

The invention claimed is:

1. A syringe drive device comprising:
a cylinder adapter;
a cylinder holding section configured to detachably and directly hold a first syringe or the cylinder adapter;
a piston operating section configured to detachably engage a piston inserted in a first cylinder of the first syringe or a piston inserted in a second cylinder of a second syringe held by the cylinder adapter; and
a piston drive section configured to move the piston operating section along a central axis of the piston to thereby move the piston in a direction in which the piston is pushed into the respective syringe or a direction in which the piston is pulled out from the respective syringe; and
wherein the cylinder adapter includes a projection and a recess, a distance between the projection and the recess being equal to a difference between a length from a tip end of the first cylinder to a flange of the first cylinder and a length from a tip end of the second cylinder to a flange of the second cylinder.

2. The syringe drive device of claim 1, wherein the piston drive section includes a pair of drive members provided on both sides of the cylinder holding section so as to extend along the central axis,
wherein rear ends of the drive members are coupled with the piston operating section, and the drive members are configured to move along the central axis, and
wherein the cylinder holding section and the cylinder adapter are configured to respectively hold the first cylinder and the second cylinder at positions such that a gasket on the end of the corresponding piston at a most forward position of piston is located at a position corresponding to front ends of the drive members.

3. The syringe drive device of claim 2, further comprising:
gears; and
a power source configured to transmit a rotation force to the gears,
wherein the drive members are racks respectively engaged with the gears, and the rotation of the gears moves the racks linearly along in a direction parallel to the central axis.

4. The syringe drive device of claim 3, wherein the cylinder holding section is configured such that at least a part of the first cylinder will be situated above a plane which includes central axes of the racks, and
the cylinder adapter is configured such that at least a part of the second cylinder will be situated above the plane which includes the central axes of the racks.

5. The syringe drive device of claim 4, wherein the cylinder adapter is configured such that a height position of a solution port of the second cylinder is the same as a height position of a solution port of the first cylinder held by the cylinder holding section.

6. The syringe drive device of claim 1, wherein the piston drive section includes a pair of drive members provided on both sides of the cylinder holding section so as to extend along the central axis,
wherein rear ends of the drive members are coupled with the piston operating section, and the drive members are configured to move along the central axis, and
wherein the cylinder holding section and the cylinder adapter are configured to respectively hold the first cylinder and the second cylinder at positions such that a gasket on the end of the corresponding piston at a most forward position of the piston is located at a position behind front ends of the drive members.

7. The syringe drive device of claim 1, further comprising a piston adapter for holding the piston of the second syringe,
wherein the piston adapter is configured to engage the piston operating section and the piston of the second syringe held by the syringe adapter.

8. The syringe drive device of claim 1, wherein said cylinder adapter is configured such that a position of the tip end side of the second cylinder held by said cylinder adapter in said cylinder holding section is the same as a position of the tip end side of the first cylinder held directly by said cylinder holding section.

9. A medication dispensing apparatus comprising a syringe drive device holding section configured to detachably hold a syringe drive device,
wherein the syringe drive device is configured to interchangeably operate a first syringe including a first cylinder and a second syringe including a second cylinder having a shape different from the first cylinder, and the syringe drive device includes
(i) a cylinder holding section configured to detachably and directly hold the first syringe,
(ii) a piston operating section configured to detachably engage a piston inserted in the first cylinder or the second cylinder,
(iii) a piston drive section configured to move the piston operating section along a central axis of the piston to thereby move the piston in a direction in which the piston is pushed into the respective syringe or a direction in which the piston is pulled out from the respective syringe, and
(iv) a cylinder adapter configured to be loaded in the cylinder holding section and configured to detachably hold the second cylinder,
wherein the cylinder adapter is configured such that a position of a tip end side of the second cylinder held by the cylinder adapter in the cylinder holding section is the same as a position of a tip end side of the first cylinder held in the cylinder holding section,
wherein the medication dispensing apparatus further comprises:
a container holding section configured to detachably hold a medicinal solution container;
a movable section provided with the syringe drive device holding section on one end thereof and the container holding section on another end thereof, the movable section being configured to move the syringe drive device and the container holding section toward and away from each other;

a pedestal section configured to rotatably support the movable section between the syringe drive device holding section and the container holding section; and a rotation drive section configured to rotate the movable section at a first position at which the syringe drive device holding section is positioned on a lower side and the container holding section is positioned on an upper side, and a second position at which the container holding section is positioned on the upper side and the syringe drive device is positioned on the lower side.

10. A system comprising:

a first syringe including a first cylinder with a flange and a piston inserted in the first cylinder;

a second syringe including a second cylinder with a flange and a piston inserted in the second cylinder, wherein a length from a tip end of the second cylinder to the flange of the second cylinder is different from a length of a tip end of the first cylinder to the flange of the first cylinder; and a syringe drive device for interchangeably operating the first syringe and the second syringe, the syringe drive device which includes (i) a cylinder adapter for holding the second cylinder of the second syringe, (ii) a cylinder holding section configured to detachably and directly hold the first syringe or the cylinder adapter, (iii) a piston operating section configured to detachably engage the piston inserted in the first cylinder of the first syringe held by the cylinder holding section or the piston inserted in the second cylinder of the second syringe held by the cylinder adapter, and (iv) a piston drive section configured to move the piston operating section along a central axis of the piston to thereby move the piston in a direction in which the piston is pushed into the respective syringe or a direction in which the piston is pulled out from the respective syringe, wherein said cylinder adapter is configured such that a position of the tip end side of the second cylinder held by said cylinder adapter in said cylinder holding section is the same as a position of the tip end side of the first cylinder held directly by said cylinder holding section.

11. The system of claim 10, wherein the cylinder adapter includes a projection and a recess, a distance between the projection and the recess being equal to the difference between the length from the tip end of the first cylinder to the flange of the first cylinder and the length from the tip end of the second cylinder to the flange of the second cylinder.

12. The system of claim 10, wherein the piston drive section includes a pair of drive members provided on both sides of the cylinder holding section so as to extend along the central axis, wherein rear ends of the drive members are coupled with the piston operating section, and the drive members are configured to move along the central axis, and wherein the cylinder holding section and the cylinder adapter are configured to respectively hold the first cylinder and the second cylinder at positions such that a gasket on the end of the corresponding piston at a most forward position of the piston is located at a position corresponding to front ends of the drive members.

13. The system of claim 12, further comprising:

gears; and a power source configured to transmit a rotation force to the gears, wherein the drive members are racks respectively engaged with the gears, and the rotation of the gears moves the racks linearly along in a direction parallel to the central axis.

14. The system of claim 13, wherein the cylinder holding section is configured such that at least a part of the first cylinder will be situated above a plane which includes central axes of the racks, and the cylinder adapter is configured such that at least a part of the second cylinder will be situated above the plane which includes the central axes of the racks.

15. The system of claim 14, wherein the cylinder adapter is configured such that a height position of a solution port of the second cylinder is the same as a height position of a solution port of the first cylinder held by the cylinder holding section.

16. The system of claim 10, wherein the piston drive section includes a pair of drive members provided on both sides of the cylinder holding section so as to extend along the central axis, wherein rear ends of the drive members are coupled with the piston operating section, and the drive members are configured to move along the central axis, and wherein the cylinder holding section and the cylinder adapter are configured to respectively hold the first cylinder and the second cylinder at positions such that a gasket on the end of the corresponding piston at a most forward position of the piston is located at a position behind front ends of the drive members.

17. The system of claim 10, further comprising a piston adapter for holding the piston of the second syringe, wherein the piston adapter is configured to engage the piston operating section and the piston of the second syringe held by the syringe adapter.

18. The system of claim 10, wherein the cylinder adapter includes a projection and a recess, a distance between the projection and the recess being equal to the difference between the length from the tip end of the first cylinder to the flange of the first cylinder and the length from the tip end of the second cylinder to the flange of the second cylinder, wherein the cylinder holding section includes a groove which engages the flange of the first cylinder, and the projection of the cylinder adapter engages the groove of the cylinder holding section, and wherein said cylinder adapter is configured such that a position of the tip end side of the second cylinder held by said cylinder adapter with the projection of the cylinder adapter engaged in the groove of the cylinder holding section is the same as a position of the tip end side of the first cylinder held directly by said cylinder holding section with the flange of the first cylinder engaged in the groove of the cylinder holding section.

\* \* \* \* \*